US008525093B2

(12) United States Patent
Bachalo et al.

(10) Patent No.: US 8,525,093 B2
(45) Date of Patent: Sep. 3, 2013

(54) AUTOMATIC SET-UP FOR INSTRUMENT FUNCTIONS

(75) Inventors: William D. Bachalo, Los Altos Hills, CA (US); Khalid M. Ibrahim, Blue Bell, PA (US); Gregory Allan Payne, Richland, WA (US)

(73) Assignee: Artium Technologies, Inc., Sunnyvale, CA (US)

( * ) Notice: Subject to any disclaimer, the term of this patent is extended or adjusted under 35 U.S.C. 154(b) by 1114 days.

(21) Appl. No.: 12/485,884

(22) Filed: Jun. 16, 2009

(65) Prior Publication Data

US 2009/0312988 A1 Dec. 17, 2009

Related U.S. Application Data

(62) Division of application No. 11/508,577, filed on Aug. 22, 2006, now Pat. No. 7,564,564.

(51) Int. Cl.
*H03G 3/20* (2006.01)
*H01J 40/14* (2006.01)

(52) U.S. Cl.
USPC .............. 250/214 AG; 250/207; 356/484

(58) Field of Classification Search
USPC ............... 250/214 AG, 207; 356/28.5, 450, 356/484–486
See application file for complete search history.

(56) References Cited

U.S. PATENT DOCUMENTS

| | | | |
|---|---|---|---|
| 3,966,324 A | 6/1976 | Iten | |
| 4,329,054 A | 5/1982 | Bachalo | |
| 4,540,283 A | 9/1985 | Bachalo | |
| 4,697,922 A | 10/1987 | Gunter, Jr. et al. | |
| 4,700,129 A | 10/1987 | Yoshizawa et al. | |
| 4,807,990 A | 2/1989 | Keefer | |
| 4,838,687 A | 6/1989 | Pfeifer | |
| 4,854,705 A | 8/1989 | Bachalo | |

(Continued)

FOREIGN PATENT DOCUMENTS

| | | |
|---|---|---|
| DE | 199 54 702 A1 | 5/2001 |
| EP | 1 855 081 A1 | 11/2007 |
| WO | WO 01/36937 A1 | 5/2001 |

OTHER PUBLICATIONS

Black, et al., "Laser-Based Techniques for Particle-Size Measurement: A Review of Sizing Methods and their Industrial Applications," Prog. Energy Combust. Sci., vol. 22, No. 3, (1996), pp. 267-306.

(Continued)

*Primary Examiner* — Seung C Sohn
(74) *Attorney, Agent, or Firm* — Blakely, Sokoloff, Taylor & Zafman LLP

(57) ABSTRACT

Machine-implemented methods and apparatuses to automatically set-up a signal processing system are described. The signal processing system is set to a first bandwidth. A sampling frequency of the signal processing system is set to a first sampling frequency. Next, first samples of first signals are received at the first bandwidth and the first sampling frequency. First parameters of the first signals based on the first samples are determined. Next, a second sampling frequency is determined based on the first parameters to sample second samples. The first parameters of the first signals may be a mean transit time, a minimum transit time, a mean frequency of the signals, and a standard deviation of the frequency of the signals. Next, a mixer frequency is determined based on the first parameters. A low pass filter is set based on the mixer frequency.

9 Claims, 18 Drawing Sheets

(56) References Cited

U.S. PATENT DOCUMENTS

| | | | |
|---|---|---|---|
| 4,986,659 | A | 1/1991 | Bachalo |
| 5,289,391 | A | 2/1994 | Ibrahim et al. |
| 5,296,910 | A | 3/1994 | Cole |
| 5,684,587 | A | 11/1997 | Naqwi |
| 5,784,160 | A | 7/1998 | Naqwi |
| 5,808,895 | A | 9/1998 | Ibrahim et al. |
| 6,087,656 | A * | 7/2000 | Kimmich et al. .......... 250/252.1 |
| 6,587,208 | B2 | 7/2003 | Maeda et al. |
| 6,654,102 | B1 | 11/2003 | Modares et al. |
| 6,909,561 | B2 * | 6/2005 | Buchholz ..................... 359/896 |
| 6,999,171 | B2 | 2/2006 | Kusuzawa |
| 7,081,626 | B2 * | 7/2006 | Ianakiev et al. .......... 250/363.07 |
| 7,126,694 | B1 | 10/2006 | Bachalo |
| 2004/0246549 | A1 * | 12/2004 | Buchholz ..................... 359/198 |
| 2005/0269513 | A1 * | 12/2005 | Ianakiev et al. ............... 250/362 |
| 2007/0263215 | A1 | 11/2007 | Bachalo et al. |

OTHER PUBLICATIONS

Bachalo, et al., "Development of the Phase/Doppler Spray Analyzer for Liquid Drop Size and Velocity Characterizations," AIAA/SAE/ASME 20$^{th}$ Joint Propulsion Conference, American Institute of Aeronautics and Astronautics, (Jun. 11-13, 1984), pp. 1-13.

Bachalo, et al., "Phase/Doppler Spray Analyzer for Simultaneous Measurements of Drop Size and Velocity Distributions," Optical Engineering, vol. 23, No. 5, (Sep.-Oct. 1984), pp. 583-590.

Bachalo, "Method for Measuring the Size and Velocity of Spheres by Dual-Beam Light-Scatter Interferometry," Applied Optics, vol. 19, No. 3, (Feb. 1, 1980), pp. 363-370.

Bachalo, et al., "5.0 Phase Doppler Particle Analyzer (PDPA)," A Handbook of Fluid Dynamics, (1998), 23 pgs.

Kapulla, et al., "Operation Condition of a Phase Doppler Anemometer: Droplet Size Measurements with Laser Beam Powder, Photomultiplier Voltage, Signal Gain and Signal-to-Noise Ration as Parameters," Measurement Science and Technology, vol. 17, No. 1, (Dec. 15, 2005), pp. 221-227.

Saffman, et al., "Automatic Calibration of LDA Measurement Volume Size," Applied Optics, vol. 26, No. 13, (Jul. 1, 1987), pp. 2592-2597.

Sankar, et al., "Performance Analysis of Various Phase Doppler Systems," 4$^{th}$ International Congress on Optical Particle Sizing, (Mar. 21-23, 1995), pp. 1-21.

Strakey, et al., "Phase-Doppler Interferometry with Probe-to-Droplet Size Ratios Less than Unity. I. Trajectory Errors," Applied Optics, vol. 39, No. 22, (Aug. 1, 2000), pp. 3875-3886.

Strakey, et al., "Phase-Doppler Interferometry with Probe-to-Droplet Size Ratios Less than Unity. II. Application of the Technique," Applied Optics, vol. 39, No. 22, (Aug. 1, 2000), pp. 3887-3893.

"CrystalLaser," Product Information Document, (dated prior to May 14, 2004), 7 pgs.

LexisNexis Summary for European Patent Application No. 1238258, (Sep. 11, 2002), 3 pgs.

European Search Report for European Application No. 07252775.7-2204 containing Communication relating to the Results of the European Search Report, (Sep. 27, 2007), 5 pgs.

European Search Report for European Application No. 07251979.6-2213 containing Communication relating to the Results of the European Search Report, (Aug. 13, 2007), 3 pgs.

* cited by examiner

AUTOMATIC SET-UP FOR INSTRUMENT FUNCTIONS

CROSS REFERENCE TO RELATED APPLICATION

The present application claims priority from and is a divisional application of U.S. patent application Ser. No. 11/508,577, filed Aug. 22, 2006 now U.S. Pat. No. 7,564,564.

FIELD

Embodiments of the invention relate to signal processing systems to characterize spherical objects, including particles, droplets, bubbles, and the like. More particularly, embodiments of the invention relate to the signal processing systems that characterize spherical objects, including particles, droplets, bubbles, and the like, using light scattering interferometry.

BACKGROUND

Information on size and velocity of spherical objects including particles, droplets, bubbles, etc., is important for a wide range of applications. These applications include, for example, fuel spray combustion analysis and control for the automotive industry, aircraft gas turbine combustion, inhaler manufacturing for the pharmaceutical industry, household spray systems manufacturing, agricultural pesticide application, aircraft icing analysis and control, spray nozzle manufacturing, atmospheric aerosol analysis, atmospheric studies, and various combustion related applications.

Typically, various laser light scattering interferometry techniques are used to determine the size and velocity of spherical objects, such as particles, drops, bubbles, etc. According to these techniques, spherical objects pass the intersection point of two crossed laser beams generated from the same laser. The two crossed laser beams form a sample volume at the intersection point. The light scattered by the spherical object, as it passes through the sample volume, produces an interference fringe pattern at the plan of the detector. The spatial period of the interference fringe pattern produced by the light scattered from the spherical object, as it passes through the sample volume, may be used to determine the size of the spherical object and a velocity component of the spherical object. The laser light scattering interferometry techniques may include a laser Doppler velocimetry ("LDV"), a laser Doppler anemometry ("LDA"), a phase Doppler interferometry ("PDI"), phase Doppler particle analyzer technique ("PDPA"), phase Doppler anemometer technique ("PDA").

The measurements of the size and velocity of the spherical objects involve many parameters that may change over the measurement. For example, temporal and spatial characteristics of the flow of the spherical objects may change, e.g., due to changes in droplet size distribution, and due to gradients of the flow velocity. In many applications, e.g., for gas turbine and automotive fuel sprays, and industrial spray studies, the number density and velocity of particles changes dramatically from location to location. The small particle size and random attenuation of the scattered light caused by other droplets that pass the laser beams close to the sample volume may produce low signal to noise ratio.

Generally, the phase shifts of the signals that are produced by photodetectors are measured to estimate the spatial period of the interference fringe pattern produced by the light scattered from the spherical objects. The phase shifts may vary with measurement conditions, e.g., signal frequency, gain of the photodetector, and other instrument parameters.

These parameters, e.g., varying temporal and spatial characteristics, varying number density of the particles, varying particle speed, low signal-to-noise ratio, varying phase shifts, increase measurement uncertainty, cause measurement errors, and impact the measurement accuracy and reliability. Therefore, the measurements of the size and velocity of the spherical objects require frequent attention to the measurement conditions which may be time-consuming and improper setup may leave the instrument prone to errors.

SUMMARY

Machine-implemented methods and apparatuses to automatically set-up a signal processing system are described. The signal processing system includes an instrument for measuring spherical objects. The signal processing system is set to a first bandwidth. A sampling frequency of the signal processing system is set to a first sampling frequency. First samples of first signals are received at the first bandwidth and the first sampling frequency. First parameters of the first signals based on the first samples are determined. A second sampling frequency is determined based on the first parameters to sample second samples. The first parameters of the first signals may be a mean transit time, a minimum transit time, a mean frequency of the signals, and a standard deviation of the frequency of the signals. A mixer frequency is determined based on the first parameters. A low pass filter is set based on the mixer frequency.

For one embodiment, a gain is set to a first value. The signals are received by the signal processing system. Intensities of the received signals are measured. The gain is adjusted to a second value based on the intensities.

For another embodiment, parameters of spherical objects passing through a first sample volume are determined. A probability that more than one spherical object resides at a time in the first sample volume is less than a predetermined threshold is determined based on the parameters of the spherical objects. An aperture of the signal processing system is adjusted based on the probability.

For yet another embodiment, samples of the signals are received by the signal processing system. Parameters of the samples of the signals are determined. A relative number of the samples that pass a validation criterion for each of the parameters is estimated. A measurement uncertainty of the signal processing system is determined based on the estimating.

For yet another embodiment, the signal processing system is calibrated. First signals are received by the signal processing system. First parameters of the first signals are determined to characterize components of the system. Next, second signals are received. Second parameters of the second signals are determined to characterize spherical objects. The second parameters are adjusted based on the first parameters.

Other features of the present invention will be apparent from the accompanying drawings and from the detailed description that follows below.

BRIEF DESCRIPTION OF THE DRAWINGS

The present invention is illustrated by way of example and not limitation in the figures of the accompanying drawings in which like references indicate similar elements.

DETAILED DESCRIPTION

Figure 1:
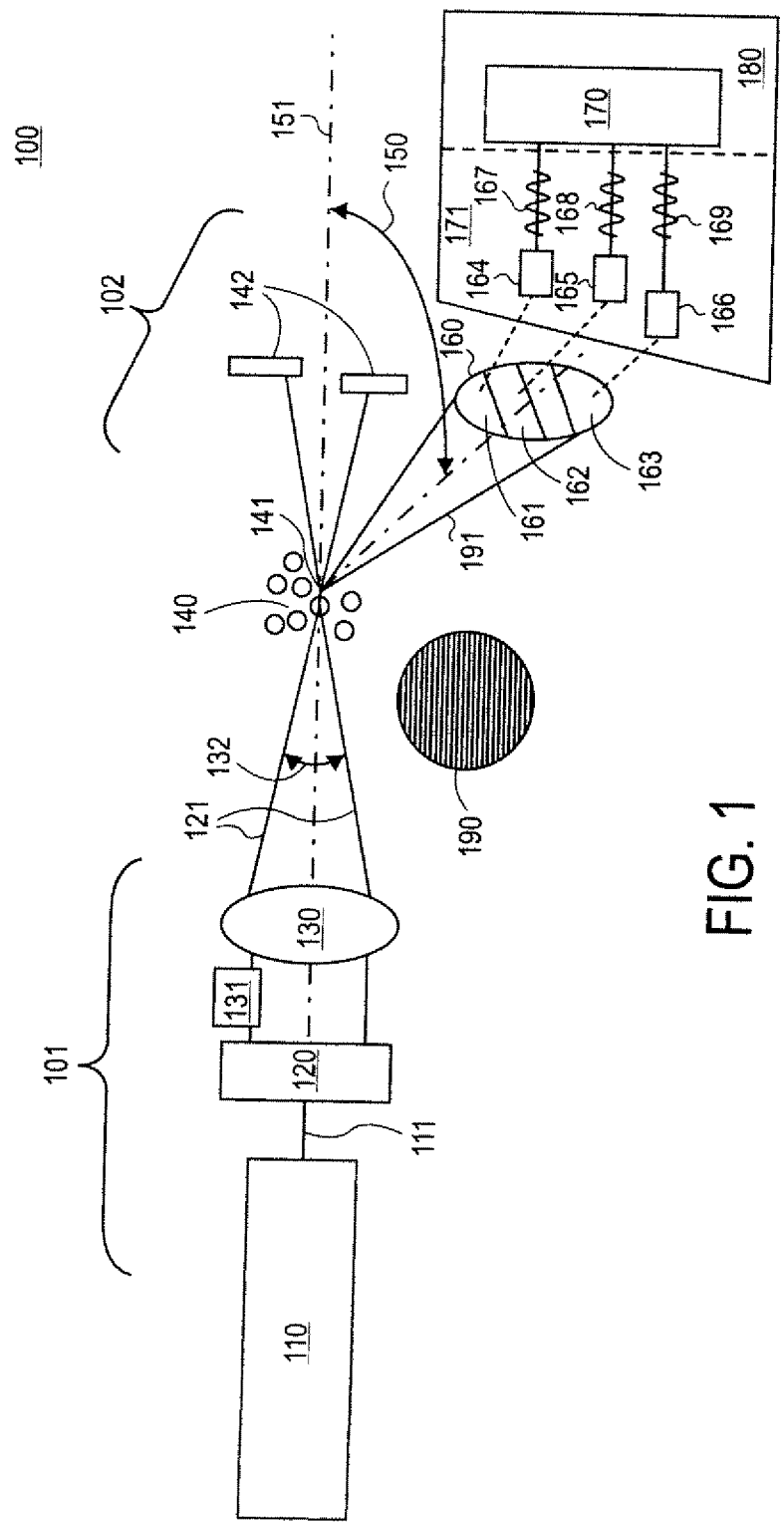
FIG. 1 shows one embodiment of a system for determining the size and velocity of spherical objects.

Machine-implemented methods and apparatuses are described to automatically set-up a signal processing and optical system to determine sizes and velocities of spherical objects, e.g., particles, drops, bubbles, and the like.

The signal processing system includes a photodetector section to convert a light scattered from a spherical object to electrical signals. The signal processing system further includes an analog section coupled to the photodetector section. The analog section has a mixer and a low pass filter. A digital section is coupled to the analog section to sample the electrical signals.

The signal processing system is a user friendly turnkey system that can be reliably set up to consistently provide accurate measurements with predictable measurement uncertainty.

The signal processing system is automatically set to a first bandwidth (e.g., a full processor bandwidth). A sampling frequency of the signal processing system is automatically set to a first sampling frequency (e.g., a maximum processor sampling frequency). Next, first samples of first signals are received at the first bandwidth and the first sampling frequency. First parameters of the first signals based on the first samples are determined. Next, a second sampling frequency is determined based on the first parameters to sample second samples. The first parameters of the first signals may be a mean transit time, a minimum transit time, a mean frequency of the signals, and a standard deviation of the frequency of the signals. Next, a mixer frequency is determined based on the first parameters. A low pass filter is set based on the mixer frequency. A decimation factor is set based on the setting of the low pass filter and the sampling frequency.

For one embodiment, a gain of the photodetector section of the signal processing system is set to a first value. The signals are received by the signal processing system. Next, intensities of the received signals are measured. The gain is adjusted to a second value based on the intensities, so that a smallest intensity of the signals is higher or equal to a detection level of the system and a largest intensity of the signals is less or equal to a saturation level of the system.

For another embodiment, parameters of spherical objects passing through a first sample volume are measured. Next, a probability that more than one spherical object resides at a time in the first sample volume is less than a predetermined threshold is determined based on the parameters of the spherical objects. Next, an aperture in front of the photodetector section is adjusted based on the probability of more than one spherical object passing the sample volume at one time.

For yet another embodiment, samples of the signals are received by the signal processing system. First parameters of the samples on photodetectors are measured. Next, a first number of the samples that pass a first parameter validation criterion is estimated. Further, second parameters of the samples of the signals on the photodetectors are measured. Next, a second number of the samples that pass a second parameter validation criterion is estimated. Next, a global measurement uncertainty of the signal processing system is determined based on the first number and the second number.

For yet another embodiment, the signal processing system is calibrated. First signals are received by the signal processing system from a calibration source. First parameters of the first signals are measured to characterize components of the system at an operating condition of a plurality of operating conditions. Next, second signals from a spherical object are received. Second parameters of the second signals are measured to characterize spherical objects. The second parameters are adjusted based on the first parameters. For one embodiment, a look up table is generated based on the first parameters at each of the plurality of the operating conditions. The second parameters are adjusted based on the look up table.

An automatic setup is configured to measure the frequency response of the different components of the system for auto-calibration of the system. Next, the automatic setup is configured to automatically set the system gain for optimum utilization of the system dynamic range. Further, the automatic setup is configured to minimize the system measurement uncertainty including the use of multiple sampling frequencies and the use of multiple phase and frequency measurements.

FIG. 1 shows one embodiment of a system for determining the size and velocity of spherical objects. A system 100 has a transmitter portion 101 and a receiver portion 102. Transmitter 101 includes a laser 110 that generates a laser beam 111, a beam splitter 120 and a focusing optics 130. As shown in FIG. 1, laser beam 111 is split by beam splitter 120 into two beams 121 of about the same intensity. As shown in FIG. 1, focusing optics 130, e.g., one or more lenses, focuses beams 121 and causes them to cross each other at an angle 132 to form a sample volume 141 having an interference fringe pattern. An enlarged view of one embodiment of the interference fringe pattern 190 formed by crossing beams 121 is shown in FIG. 1. Sample volume 141 is an overlap region of beams 121 which cross each other at angle 132, as shown in FIG. 1. For one embodiment, angle 132 depends on the size of measured particle. For one embodiment, increasing angle 132 increases the difference between the phase of light scattered by refraction and reflection, allowing more effective discrimination between refraction and reflection components of the scattered light. For one embodiment, angle 132 formed by crossing beams 121 is in the approximate range of 1 to 20 degrees. For one embodiment, each of the laser beams 121 at the overlap region has a Gaussian or other light intensity profile. For an embodiment, beam splitter 120 and focusing optics 130 of transmitter 101 are commercially available optical components known to one of ordinary skill in the art of optical transmitter manufacturing.

As shown in FIG. 1, one of the beams 121 generated by laser 110 is modulated with a frequency by a modulator 131 to provide frequency shifting. The frequency shifting is used to compress the frequency dynamic range and resolve the direction ambiguity that would occur for spherical objects passing in a reverse direction. For one embodiment, the frequency of the modulator 131 to modulate one of the laser beams 121 is in the approximate range of 20 to 60 Megahertz ("MHz"). For an embodiment, the modulator 131 modulates one of the laser beams 121 is an acousto-optical modulator. For one embodiment, the modulator 131 to modulate one of the laser beams 121 is a Bragg cell. Bragg cells are known to one of ordinary skill of optical transmitter manufacturing.

For one embodiment, each of the Gaussian laser beams 121 is first clipped to remove light on the wings of the Gaussian curve at some desired level (e.g., $I/I_o=1/e^2$) to reduce the size of the sample volume and decrease the number of signals to be processed that will ultimately be rejected in at signal validation operations. Clipping the wings of the Gaussian curve of the laser beams also helps to better define the particle detection region needed in analyzing the results for estimating particle number density and flux.

An optical receiver collecting optics 160 is positioned at an off-axis detection angle 150 from the transmitted beam direction. For one embodiment off-axis detection angle 150 is in the approximate range of 20-75 degrees from direction 151 of transmitting beams 121. The light from crossing beams 121 is scattered by spherical objects 140, e.g., particles, drops, bubbles, and the like, passing through sample volume 141 located at the intersection of the beams 121. The light from each of the two laser beams 121 scattered from one of the spherical objects 140 by various scattering mechanisms, e.g., refraction and reflection, interferes to form a spatially and temporally varying fringe pattern 191 on receiver optics 160. The collecting optics 160 of the receiver 102 collects the interference fringe pattern formed by the scattered light, partitions the interference fringe pattern into three portions 161, 162 and 163, and directs them on to a signal processor 180. Signal processor 180 includes a photodetector section 171 and a processing section 170 described in further detail below. Photodetector section 171 includes three spaced apart photodetectors 164, 165 and 166. As shown in FIG. 1, each of the photodetectors 164-166 receives a respective portion 161-163 of the interference fringe pattern produced by the light scattered from one of the spherical objects 140. For one embodiment, the detectors 164, 165 and 166 are located in the interference fringe pattern, or an image of it, and the separation between the detectors 164, 165 and 166 is known.

When the spherical object, e.g., a particle, drop, bubble, and the like, is moving, a Doppler shift in the frequency of the scattered light occurs. The difference in the Doppler frequency shift plus the imposed frequency shift by the frequency modulator between the light scattered from each of the beams 121 causes the fringe pattern to appear to move. As the interference fringe pattern sweeps past photodetectors 164-166 at the Doppler difference frequency plus the imposed frequency shift by the frequency modulator, photodetectors 164-166 produce time varying signals 167-168. For one embodiment, when the light received by photodetectors 164-166 is scattered from the spherical object due to a single dominant scattering mechanism, e.g, either a refraction, or reflection, the interference fringe pattern is periodic, e.g., a sinusoidal wave signal. The periodic interference pattern that sweeps past photodetectors 164-166 at the Doppler difference frequency produces signals 167-168 that are identical in frequency, but shifted in phase. The phase shift φ is related to the spacing of the scattered fringe pattern through the following relationship:

$$\frac{\phi}{360°} = \frac{s}{\Lambda} \qquad (1)$$

wherein s is the spacing between a pair of the photodetectors, for example, photodetectors 161 and 162, φ is the phase shift between the signals 167 and 168, and Λ is the spacing between the fringes (wavelength) of the interference pattern at the location of the photodetectors 164 and 165 and is inversely proportional to the diameter of the spherical object.

For one embodiment, the spherical object's size may be in the approximate range of 0.5 micrometers ("um") to 1000 um, for example. To measure a velocity component, any one of photodetectors 164, 165, and 166 may be used. For one embodiment, a small aperture (not shown) is used in front of the signal processor 180 (e.g., at the rear focal point of the receiver optics) to allow only light scattered by particles crossing a small region of the beam intersection to reach the photodetectors 164-166. The rest of the scattered light is blocked by light blockers 142 for safety reasons. The small aperture (not shown) may be used in the receiver lens path to minimize the noise in the signal and limit the size of the measurement volume.

Photodetectors 164, 165, and 166 are used to resolve the phase ambiguity, extend the measurement range and resolution, and to validate each of the time varying signals 167-169 for determining the size and velocity of the spherical object. As shown in FIG. 15 photodetectors 164-166 send time varying electrical signals 167-169 to processing section 170 to determine the size and velocity of spherical objects. Signal processor 180 is described in further detail below with respect to FIGS. 3-17.

Figure 2:
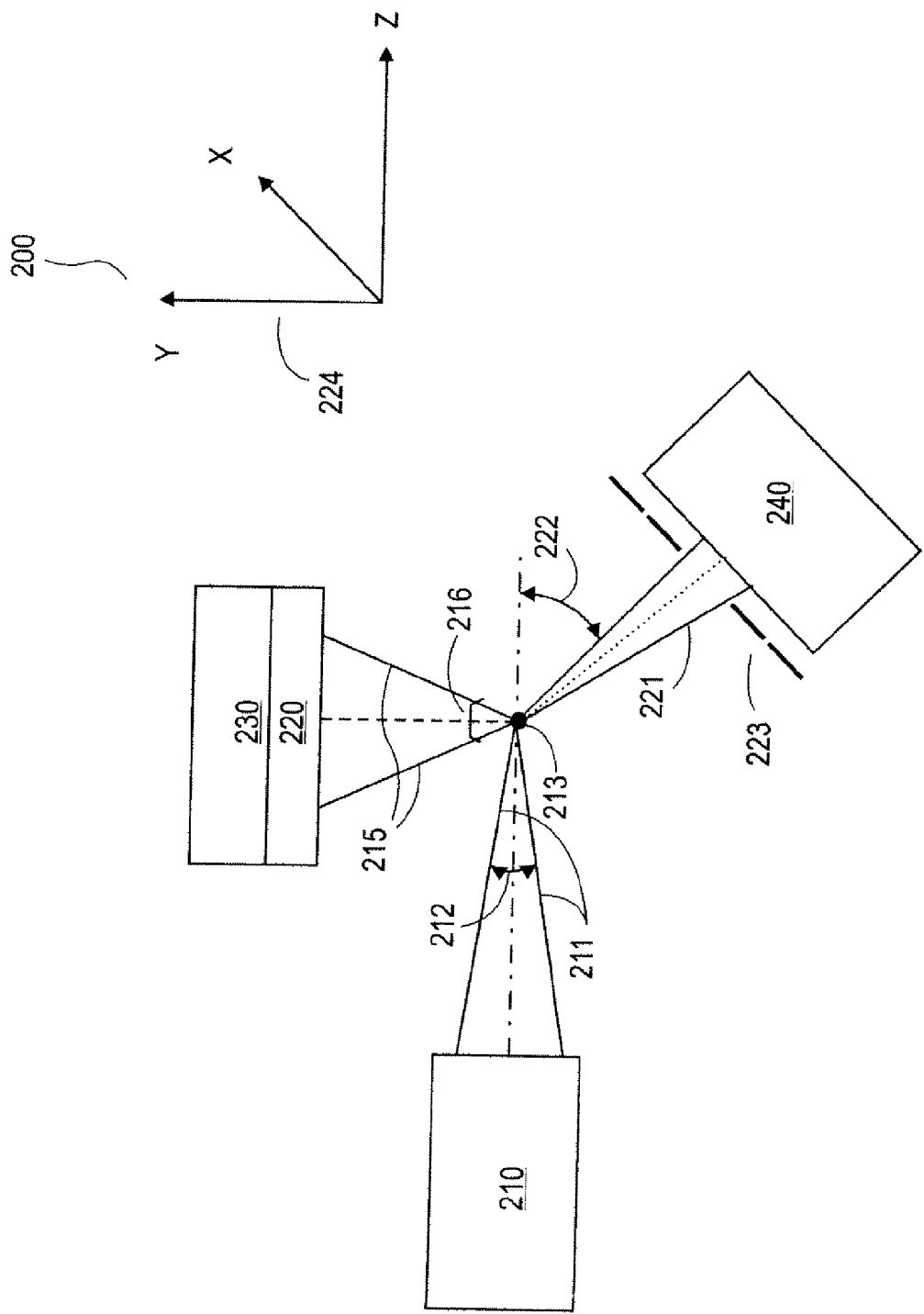
FIG. 2 shows one embodiment of an apparatus for measuring the size and up to three velocity components of a spherical object.

FIG. 2 shows one embodiment of an apparatus 200 for measuring the size and up to three velocity components of a spherical object. Beam propagation with respect to the Cartesian coordinate system 224 is shown in FIG. 2. The apparatus 200 has a transmitter 210 for generating a first pair of coherent beams 211 propagating along an axis Z in the plane ZY and crossing each other at an angle 212 to form a sample volume 213 to measure a size and an V-velocity component of a spherical object located inside the sample volume 213. The apparatus 200 also has a transmitter 220 that generates a second pair of coherent beams 215 propagating a plane ZY along an axis Y that is perpendicular to an axis Z. The beams 215 cross each other at an angle 216 to form sample volume 213 to measure a Z-velocity component of the spherical object located inside the sample volume 213. The apparatus 200 further includes a transmitter 230 that generates a third pair of coherent beams (not shown) propagating in a plane XY along axis Y. The third pair of the beams cross each other at an angle to form sample volume 213 to measure an X-velocity component of the spherical object located inside the sample volume 213. For one embodiment, the transmitter 230 is stacked on top of the 220. For one embodiment, the angles formed by each pair of coherent beams 211, 215, and 217 is in the approximate range of 1 degree to 20 degrees.

For an embodiment, each of the transmitters 210, 220, and 230 is a compact, highly efficient, commercially available diode-pumped solid-state ("DPSS") laser having substantially high pointing stability. For one embodiment, the DPSS laser models GCL-XXX-S, BCL-XXX-S, etc., supplied by CrystaLaser of Reno, Nev. may be used. More specifically, the pointing stability of the DPSS used in transmitters 210, 220, and 230 is less than about 0.02 mrad.

For an embodiment, to simultaneously measure the size and three velocity components of the spherical object, transmitters 210, 220, and 230 generate light at a first, a second, and a third wavelength, respectively. More specifically, the first, second, and third wavelengths are, for example, violet, red, and green, respectively. For another embodiment, each of the transmitters 210, 220, and 230 generate light having a first, second, and third polarization, respectively. For yet another embodiment, two transmitters 210 and 220 generate light having a first and second wavelength respectively, with the same polarization, and the transmitter 230 generates light having the first wavelengths but the polarization is different from the polarization of the transmitters 210 and 220.

For apparatus 200 of FIG. 2, the scattered light 221 from the spherical object is collected by a signal processor 240 that is configured to sense the scattered light 221, convert it to time varying electrical signals, and process the signals as described in further detail below with respect to FIGS. 3-17. As shown in FIG. 2, system 200 has a variable aperture 223 in front of signal processor 240. For one embodiment, variable aperture 223 is a movable strip-like slit aperture. For one embodiment, the strip has a plurality of slit widths at different locations along the strip. For one embodiment, the slit is formed by two movable blades that can be separated at the desired slit width. For one embodiment, signal processor 240 includes three photodetectors, wherein each of the photodetectors receives a portion of an interference fringe pattern formed by a light scattered from a spherical object and generates a time varying signal to produce a plurality of time varying signals, as described above. For an embodiment, signal processor 240 is positioned off-axis to the transmitter beams direction. The central axis of the signal processor 240 forms an angle 222 relative to a propagation axis of the first pair of beams 211.

For an embodiment, signal processor 240 is positioned off-axis to the transmitter beams direction. The central axis of the signal processor 240 forms an angle 222 relative to a propagation axis of the first pair of beams 211. For an embodiment, the angle 222 is in the approximate range of 25 to 45 degrees. For one embodiment, the angle 222 is about 30 degrees. The signal processor 240 is in a plane that passes through the crossing of the beams, and is orthogonal to the plane formed by the two crossing beams.

Figure 3A:
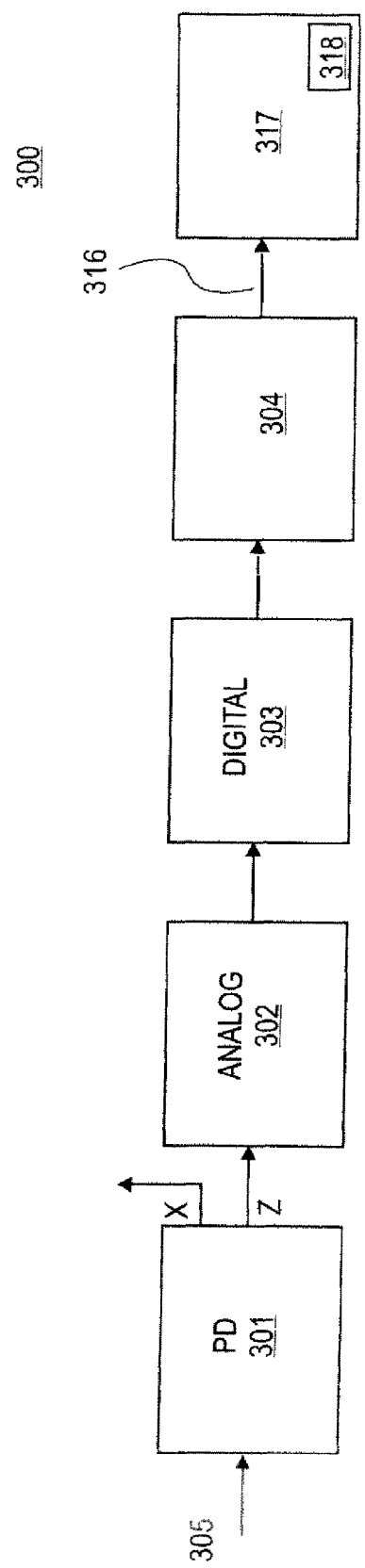
FIG. 3A shows one embodiment of a signal processor to receive and process signals to determine the size and one or more of velocity components of spherical objects.

FIG. 3A shows one embodiment of a signal processor to receive and process signals to determine the size and one or more of velocity components of spherical objects. As shown in FIG. 3, signal processor 300 includes a photodetector ("PD") section 301, analog section 302, and digital section 303. As shown in FIG. 3, optical signals 305 are collected by receiver optics (not shown) of photodetector section 301, converted to electrical signals and passed to analog section 302. For one embodiment, the receiver optics are LDV optics, LDA optics, PDI optics, PDPA optics, PDA optics, or any other optics known to one of ordinary skill in the art of the optics manufacturing. For one embodiment, the signals received from the spherical objects are Doppler burst signals. For one embodiment, the amplitude of the signals from spherical objects can vary over a wide dynamic range (over 1:10,000) from one measurement to another. For one embodiment, the gain of the photodetector section 301 is changed automatically to fit the signals having various amplitudes to a fixed input amplitude range of the signal processor.

Figure 3B:
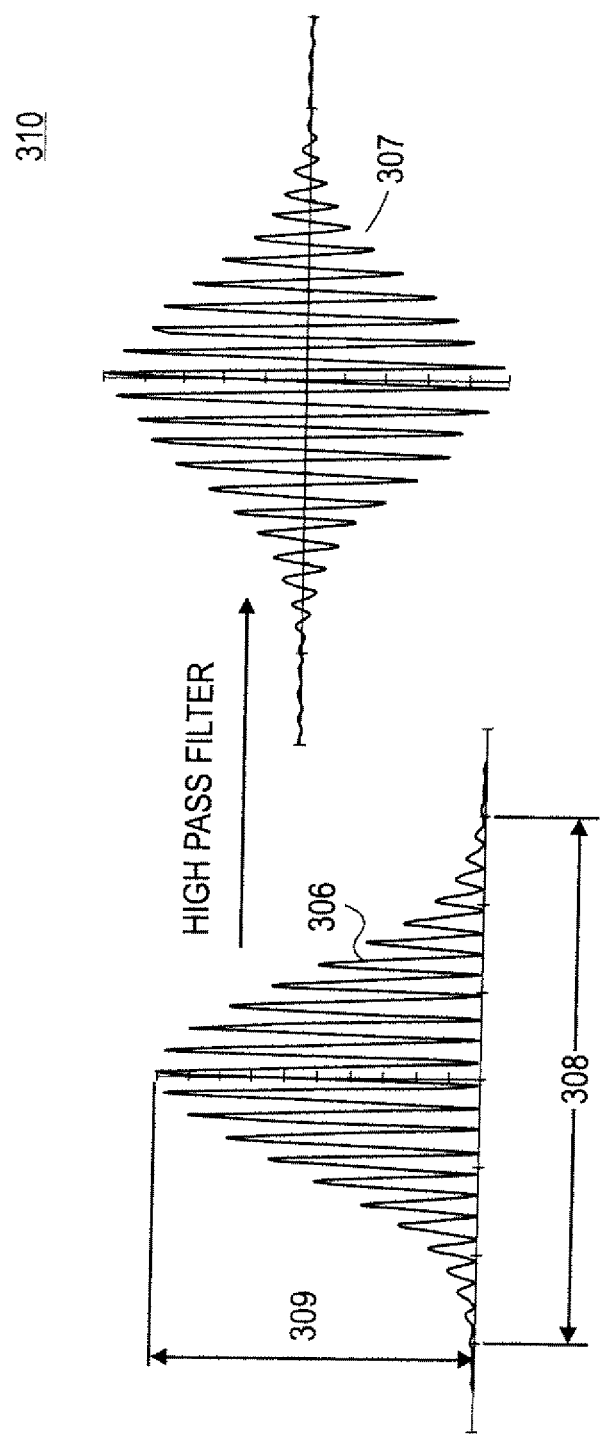
FIG. 3B shows one embodiment of a typical Doppler burst signal before and after high-pass filtering in photodetector section.

FIG. 3B shows one embodiment 310 of a typical Doppler burst signal before 306 and after 307 high-pass filtering in photodetector section 301. As shown in FIG. 3B, Doppler burst signal 306 has an envelope (e.g., a Gaussian shape envelope), amplitude 309, and width 308. As shown in FIG. 3B, burst signal 306 is modulated by a sinusoidal wave. Optical frequency shifters e.g., Bragg cells, are used to modulate the frequency of the burst signal. Modulating the burst signal frequency is used to detect the direction of motion of spherical objects, as described above with respect to FIG. 1. Modulating the burst signal frequency is also used to reduce the relative frequency range of the burst signals. The Doppler frequency shift is determined by the droplet velocity component in the plane of two crossing laser beams, as described above with respect to FIGS. 1 and 2. The frequencies of the signal bursts are determined by the sum of the Doppler frequency shift and the frequency of the optical shifter. The signal frequencies may vary from about 5 MHz to more than 200 MHz. For one embodiment, the amplitude 309 of the burst signal 306 can vary over a dynamic range of about 1:2500. The transit time $\tau$ of the signal burst 306 is determined by the width 308 of the signal burst. The transit time $\tau$ of the signal burst 306 determined by the speed v of the spherical object and the diameter w of the focused laser beam at the sample volume according to the formula:

$$\tau = w/v \qquad (2)$$

For one embodiment, transit time $\tau$ can vary in the approximate range from 10 nanoseconds ("ns") to more than 10 milliseconds ("msec").

Referring back to FIG. 3, photodetector section 301 has two outputs. Electrical signals from output X may be used to measure peak intensity and average power to adjust the gain of the photodetector section 301, as described in further detail below with respect to FIGS. 4, 6, and 12. Electrical signals from output Z are fed to analog section 302.

Figure 4:
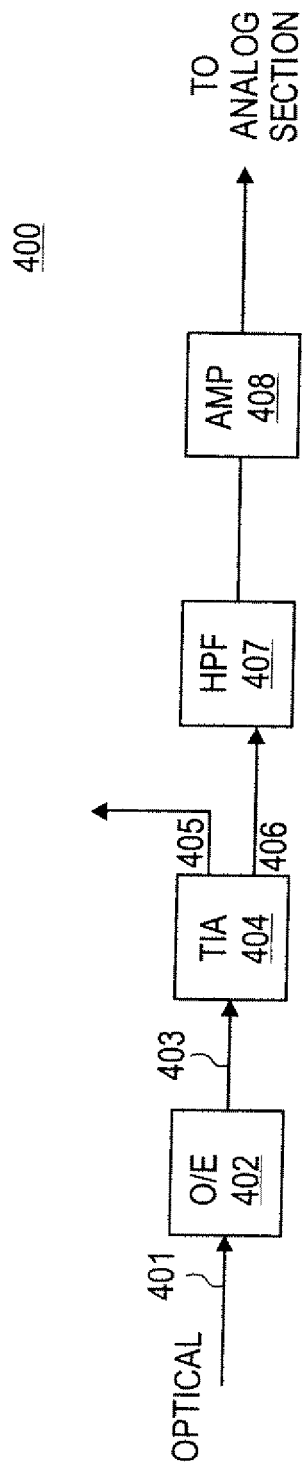
FIG. 4 shows one embodiment of photodetector section of a signal processor to determine the size and one or more velocity components of the spherical objects.

FIG. 4 shows one embodiment 400 of photodetector section 301 of a signal processor to determine the size and one or more velocity components of the spherical objects.

As shown in FIG. 4, optical signals 401 are received by one or more photodetectors 402. Photodetectors 402 convert optical signals 401 into electrical burst signals 403, e.g., current.

As shown in FIG. 4, electrical signals 403 are then fed to a transimpedance amplifier ("TIA") 404. Transimpedance amplifier 404 is used to convert a photodetector current to voltage. As shown in FIG. 4, output 405 of TIA 404 may be used to measure e.g., an average power of the signal, and peak intensity of the signal. The peak intensity and the average power of the signals may be used for adjustment of the gain of one or more photodetectors 402, as described in further detail below. For one embodiment, photodetectors 402 are photo-multiplier tubes ("PMTs"). For one embodiment, the gain of photodetector section 301 can be adjusted by changing the bias high voltage of the PMTs. For another embodiment, photodetectors 402 are fixed gain photodetectors, e.g., PIN photodetectors and avalanche photodetectors ("APD") For one embodiment, the gain of the fixed gain photodetectors is adjusted by placing one or more variable optical attenuators (not shown) in front of the one or more photodetectors 402. As shown in FIG. 4, signals from output 406 of TIA 404 are filtered by high-pass filter ("HPF") 407 ad then pre-amplified, e.g., by 15 dB, using pre-amplifier 408. After pre-amplifier 408, electrical signals are input to analog section 303.

Referring back to FIG. 3, analog section 303 is used to change the signal processor frequency bandwidth to fit the actual frequency bandwidth of the input Doppler signals to optimize the signal processor performance and to maximize the signal-to-noise ratio ("SNR").

Figure 5:
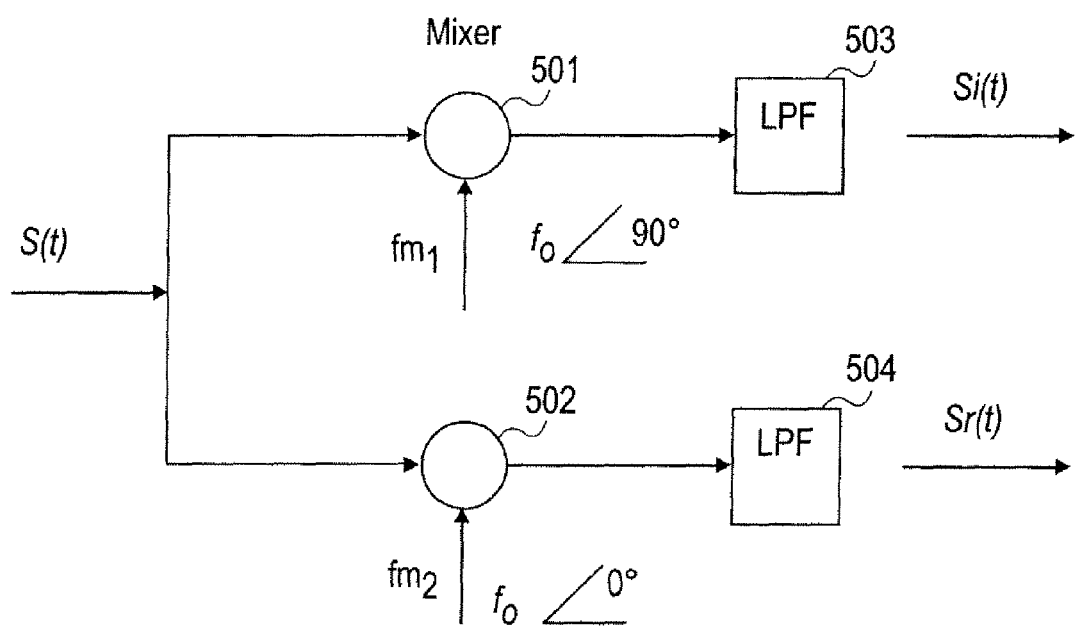
FIG. 5 shows one embodiment of an analog section of a signal processor to determine the size and one or more velocity components of the spherical objects.

FIG. 5 shows one embodiment 500 of an analog section 303 of a signal processor to determine the size and one or more velocity components of the spherical objects. As shown in FIG. 5, electrical signals S(t) from photodetector section 301 are split and fed to quadrature mixers 501 and 502. For one embodiment, electrical signals S(t) are amplified in the analog section 302 by an amplifier (not shown) before being fed to quadrature mixers 501 and 502 to provide immunity to electromagnetic interference ("EMI") and ground loops. As shown in FIG. 5, mixer 501 is driven by a quadrature local oscillator $f_0 \angle 90$. Mixer 502 is driven by an in-phase local oscillator $f_0 \angle 0$. The output of mixer 501 is applied to LPF 503 to generate quadrature signals Si(t), and output of mixer 502 is applied to LPF 504 to generate in-phase signals Sr(t).

Quadrature mixers 501 and 502 and low pass filters 503 and 504 are used to adjust the frequency bandwidth of the signal processor to an actual input frequency bandwidth of incoming Doppler signals. For one embodiment, the actual frequency bandwidth of Doppler signals does not exceed 0.1 of the full bandwidth of the signal processor. For example, the full bandwidth of the signal processor may be more than 100 MHz, and the actual bandwidth of the Doppler signals may be less than 10 MHz.

Generally, the mixer produces the sum and difference of the signal frequency and the mixer frequency as shown in the expressions below.

$$f^+ = (f_s + f_D) + f_o \quad (3)$$

$$f^- = (f_s + f_D) - f_o \quad (4)$$

where the signal frequency is a sum of the optical shifter frequency $f_s$ and the Doppler difference frequency $f_D$, and $f_0$ is the mixer frequency. As shown in FIG. 5, mixer 501 (or the mixer $f_m1$) produces the sum $f^+$ and difference $f^-$ of the signal frequency and the frequency $f_0$ of the mixer 501. Mixer 502 (or the mixer $f_{m2}$) produces the sum $f^+$ and difference $f^-$ of the signal frequency and mixer frequency $f_0$ (which has the same frequency $f_0$ of the mixer 501 at a quadrature or 90 degrees phase shift), as shown in FIG. 5. The sum frequency $f^+$ of the mixer is removed by a respective low pass filter, As shown in FIG. 5, the sum frequency of mixer 501 is removed by low pass filter 503, and the sum frequency of mixer 502 is removed by low pass filter 504. The mixer frequency $f_0$ of mixers 501 and 502 is adjusted and the low pass filters 503 and 504 are set to maximize the SNR of the incoming signals S(t). For one embodiment, the mixer frequency $f_0$ of the mixers 501 and 502 is software selectable from a plurality of frequencies. For one embodiment, mixer frequency $f_0$ of the mixers 501 and 502 is selected from the set of discrete values, e.g., 40 MHz, 80 MHz, 36 MHz, and 30 MHz. For another embodiment, frequency $f_0$ of the mixers 501 and 502 is selectable from the frequencies in the approximate range of 1 MHz to 500 MHz using a state of the art digital frequency synthesizer Mixer frequencies may be provided internally, or externally. The use of external mixer frequency allows operation of all the mixers for multi-channel applications with the frequency used for optical shifter drivers, e.g., Bragg cell drivers. This provides more accurate near zero velocity measurements. As shown in FIG. 5, quadrature signals $S_i(t)$ from LPF 503 and in-phase signals $S_r(t)$ from LPF 504 are fed to digital section 303.

Referring back to FIG. 3, quadrature signals $S_i(t)$ and in-phase signals $S_r(t)$ from analog section 302 are sampled in digital section 303 with a sampling frequency. For one embodiment, a transit time τ, e.g., a minimum transit time, and a mean transit time, of the Doppler burst signals sets the sampling frequency. Digital section 303 provides sampling and digitizing of the analog electrical signals using an adaptive sampling technique, as described below with respect to FIGS. 6, 7-11. Digital section 303 also provides assembly of data packets, as described in further detail below with respect to FIG. 6.

Digital section 303 can sample the analog signals with samplers that may have either one bit or multibit quantization. For multibit quantization signal is digitized with a range of resolution on amplitude. The sampling frequency of an analog to digital converter of the digital section 303 samples the analog signals at a frequency greater than twice of the signal frequency to satisfy the Nyquist criteria. Nyquist criteria are known to one of ordinary skill in the art of electronics devices manufacturing. To accommodate the wide dynamic range of signal burst transit time, the digital section 303 of the signal processor 300 is supported with a wide range of sampling frequencies. The analog signals from analog section 302 are sampled at a rate that allows obtaining a sufficient number of samples for accurate frequency and phase measurements. For example, the sufficient number of samples for the frequency measurements may be such that the frequency measurement accuracy is within about +/−0.1% margins. For example, the sufficient number of samples for the phase measurements may be such that the phase measurement accuracy is within about +/−2 degrees. For the optimum measurement accuracy, sampling is performed over the full signal burst. For one embodiment, to obtain the sufficient number of samples to accurately determine the frequency and phase of the signals, the sampling frequency of digital section 303 is varied depending on the transit time (e.g., mean transit time, and minimum transit time) of signal bursts. For one embodiment, the sampling frequency of digital section 303 is software selectable from a plurality of frequencies. For one embodiment, the sampling frequency of digital section is obtained by a subsequent division of the master clock frequency of 160 MHz by 2. For one embodiment, the sampling frequency ranges from about 160 MHz to about 1.25 MHz. For one embodiment, the digitized, sampled data signal may be applied to a digital burst detector to determine when a burst signal is present in the continuously sampled record, as described below with respect to FIG. 6. For one embodiment, the signal burst detector output is combined with an analog burst detector output with a pre-selected threshold voltage level and then used as an input to the adaptive sampling circuitry, as described below with respect to FIG. 6. With the detection of a Doppler burst signal, a data packet is assembled. That is, the sampled data for each Doppler burst signal is packed into a single data packet.

Because the transit time for burst signals may vary over a wide dynamic range (in some cases in excess of 1:100), an adaptive sampling technique is employed for sampling the data. The adaptive sampling technique provides a variable number of samples in each data packet that is adaptive to the width (e.g., transit time) of the burst signal. That is, the size of the data packet is variable. To avoid problems with synchronization errors while handling the data packets with variable sizes, a synchronizing technique may be employed. For example, each variable size data packet may have a number of synchronization words. Additionally, each data packet may be stamped with two numbers. The first number may be the total number of words in the data packet. The second number may be a channel (e.g., component) number from which the data packet is originated. Other parameters that are relevant to the setting of the signal processor may be measured and assembled into the data packet. These parameters may include, for example, the peak signal intensity, transit time, time of arrival, elapsed time, and external input data.

As shown in FIG. 3, a data packet is transferred from digital section 303 computer interface 304, e.g., a high speed I/O card. For example, the data packet may be transferred to a main FIFO on the I/O card. Further, the data packet may be transferred via a PCI interface 316 to a memory 318 of a computer 317 for processing using the complex Fourier transform to obtain the signal frequency and phase information.

Computer 317 unpacks each data packet to recover the sampled data and the other relevant information (e.g., time of arrival, transit time, elapsed time, peak signal intensity, and external input data) contained in the data packet. The sampled data is then processed and used to compute the frequency and the phase. For one embodiment, computer 317 processes the sampled data using a Fast Fourier Transform algorithm. For another embodiment, computer 317 processes the sampled data using an autocorrelation plus counting approach. To improve the frequency and phase resolution, validation criteria may be used to accept or reject each data packet. The validation criteria may include a signal-to-noise Ratio (SNR) of the sampled data that is computed using, e.g., the Fourier analysis method. To measure the size of the spherical objects, the SNR for each of the three photodetector channels is computed and used to validate the measurement.

Figure 6:
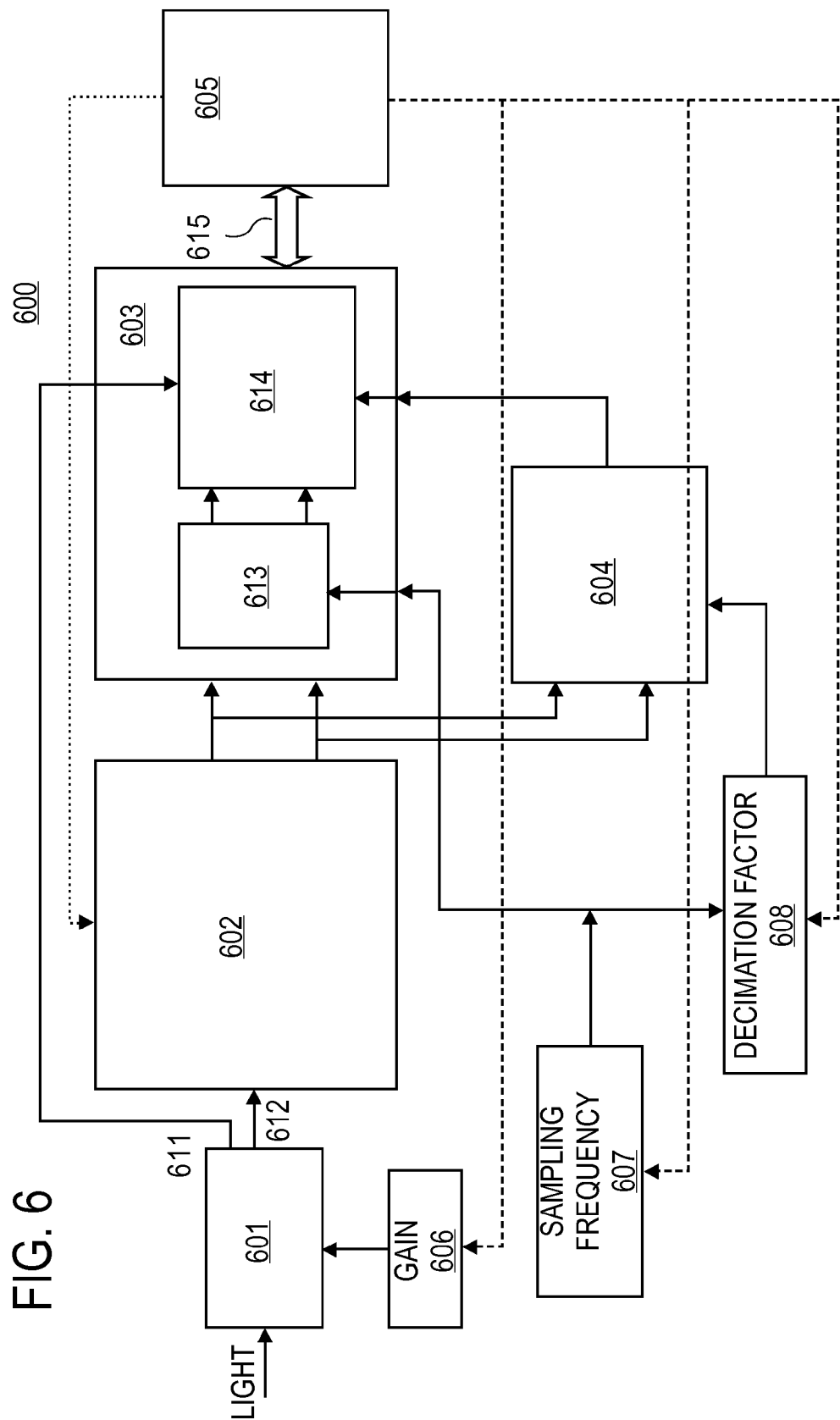
FIG. 6 shows a block diagram of one embodiment of a signal processor to determine the size and velocity of spherical objects.

FIG. 6 shows a block diagram of one embodiment of a signal processor 600 to determine the size and velocity of spherical objects. As shown in FIG. 6, signal processor 600 includes a photodetector section 601, an analog section 602, a digital section 603, and a digital/analog burst detector section 604. As shown in FIG. 6, digital section 603 is coupled to a processing unit 605, e.g., a microcontroller. For one embodiment, processing unit 605 can be a microprocessor, such as an Intel Pentium® microprocessor, Motorola Power PC® microprocessor, Intel Core™ Duo processor, AMD Athlon™ M processor, Turion™ processor, AMD Sempron™ processor, and any other microprocessor. For one embodiment, the processing unit of signal processor 600 includes a CPU, a microcontroller, a digital signal processor, a microprocessor, a personal computer ("PC"), or any combination thereof.

For one embodiment, processing unit 605 includes a general purpose computer system based on the PowerPC®, Intel Core™ Duo, AMD Athlon™, AMD Turion™ processor, AMD Sempron™, HP Pavilion™ PC, HP Compaq™ PC, and any other processor families. As shown in FIG. 6, processing unit 605 is coupled to digital section 603 by a bus 615. For one embodiment, bus 615 can be Peripheral Component Interconnect ("PCI") bus, PCI-X, PCI Express, Universal Serial Bus ("USB"), IEEE 1394 bus (e.g., Firewire®), or any other bus known to one of ordinary skill in the art.

Photodetector section 601 converts light scattered from a spherical object to electrical signals. The gain of the photodetector section 601 is adjustable, as described in further detail below with respect to FIG. 12. For one embodiment, photodetector section 601 includes one or more photomultiplier tubes (PMTs). For another embodiment, photodetector section 601 includes one or more photodetectors having a fixed gain, e.g., PIN and APD photodiodes. Output 611 provides signals from photodetector section 601 to digital section 603 to measure, e.g., signal peak intensity. Output 612 provides signals from photodetector section 601 to analog section 602.

Analog section 602 has at least one low pass filter and at least one mixer, as described above with respect to FIG. 5. The signal processor frequency bandwidth is adjusted by changing the frequency of the mixer and selecting the appropriate LPF to optimize the SNR, as described in further detail below with respect to FIGS. 7-11. The output signals from analog section 602 (e.g., in phase and quadrature signals) are fed to digital section 603 and to burst detector section 604, as shown in FIG. 6. Signals (e.g., in-phase and quadrature signals) from analog section 602 are sampled by quadrature sampler/digitizer 613 in digital section 603 at a sampling frequency. For one embodiment, the transit time (e.g., minimum transit time) of the Doppler burst signals sets the sampling frequency of the quadrature sampler/digitizer 613. To determine the transit time, the sampled data is first applied to the burst detector 604. With the detection of each burst signal, a data packet is assembled in portion 614. For one embodiment, portion 614 includes FIFO registers to acquire samples. For one embodiment, portion 614 is configured to measure transit times of the burst signals, burst signal peak intensities, and arrival times of the burst signals. Because the transit time of the burst signals can vary over a wide dynamic range (e.g., more than 1:100), an adaptive sampling technique is employed. That is, using the adaptive sampling technique a data packet can be generated, so that the size of the data packet depends on the transit time of the burst signal. Other parameters that are relevant to the setting of the signal processor can be also measured and assembled into the data packet. These parameters include the peak signal intensity, transit time, and time of arrival.

For one embodiment, digital section 603 performs measurement of the intensity of the raw signal from photodetector section 601. For an embodiment, digital section 603 generates analog and digital control signals for analog section 602 and digital section 603. Analog control signals may include analog burst detector thresholds provided to burst detector section 604 and gain controls (e.g., high voltage controls) provided to photodetector section 601. Digital control signals may include signals for selecting a sampling frequency, a mixer frequency, and a LPF.

Burst detector section 604 includes an analog burst detector and a digital burst detector. The digital burst detector of section 604 can sample signals from analog section 602 at another sampling frequency. The Doppler burst signals are detected over a wide range of signal bandwidth, SNR and amplitude. The digital burst detector interrogates short sections of the sampled signal to estimate the SNR to determine the presence of the signal bursts. For one embodiment, the sampled data are sampled at twice of the signal bandwidth to ensure that consecutive samples of the noise are statistically independent and to compute an accurate estimate of the short record SNR. For one embodiment, the sampling frequency of the quadrature sampler/digitizer is determined by the minimum transit time of the signal bursts. The sampling frequency can be more than twice of the signal bandwidth. For this reason, to ensure reliable operation of the digital burst detector, the sampled data are decimated before being applied to the digital burst detector. For one embodiment, a decimation factor is defined as the ratio of the sampling frequency of the quadrature sampler/digitizer 613 to the digital burst detector sampling frequency. For one embodiment, the decimation factor is determined by dividing the sampling frequency of the quadrature sampler/digitizer (determined, e.g., by the minimum transit time of the signal bursts) divided by twice the signal bandwidth. The analog burst detector may be also used in burst detector section 604 in conjunction with the digital burst detector to determine the beginning and the end of each Doppler burst.

As shown in FIG. 6, processing unit 605 is coupled to photodetector section 601, analog section 602, digital section 603, and burst detector section 604. As shown in FIG. 6, processing unit 605 is coupled to photodetector section 601 to adjust gain 606 of photodetector section 601 using methods described below with respect to FIG. 12. For one embodiment, the gain of photodetector section 601 is adjusted by changing a high voltage of the PMTs. For another embodiment, the gain of photodetector section 601 is adjusted by varying the attenuation of one or more variable optical attenuators placed in front of the photodetectors having a fixed gain, e.g., PIN and APD photodetectors. As shown in FIG. 6, processing unit 605 is coupled to analog section to adjust a mixer frequency and select a low pass filter using methods described below with respect to FIGS. 7-11. As shown in FIG. 6, processing unit 605 is coupled to digital section to determine parameters of the samples of the signals and provide the sampling frequency 607 using methods described below with respect to FIGS. 7-11. Processing unit 605 is coupled to burst detector section 604 to provide a decimation factor using methods described below with respect to FIGS. 7-11.

For one embodiment, signal processor 600 moves automatically from one measurement location to another, performs automatic set-ups for measurement functions at each measurement location, and then acquires data using methods described below. For one embodiment, signal processor 600 is incorporated in a single package. For one embodiment, signal processor 600 is a system-on-chip ("SOC").

Figure 7:
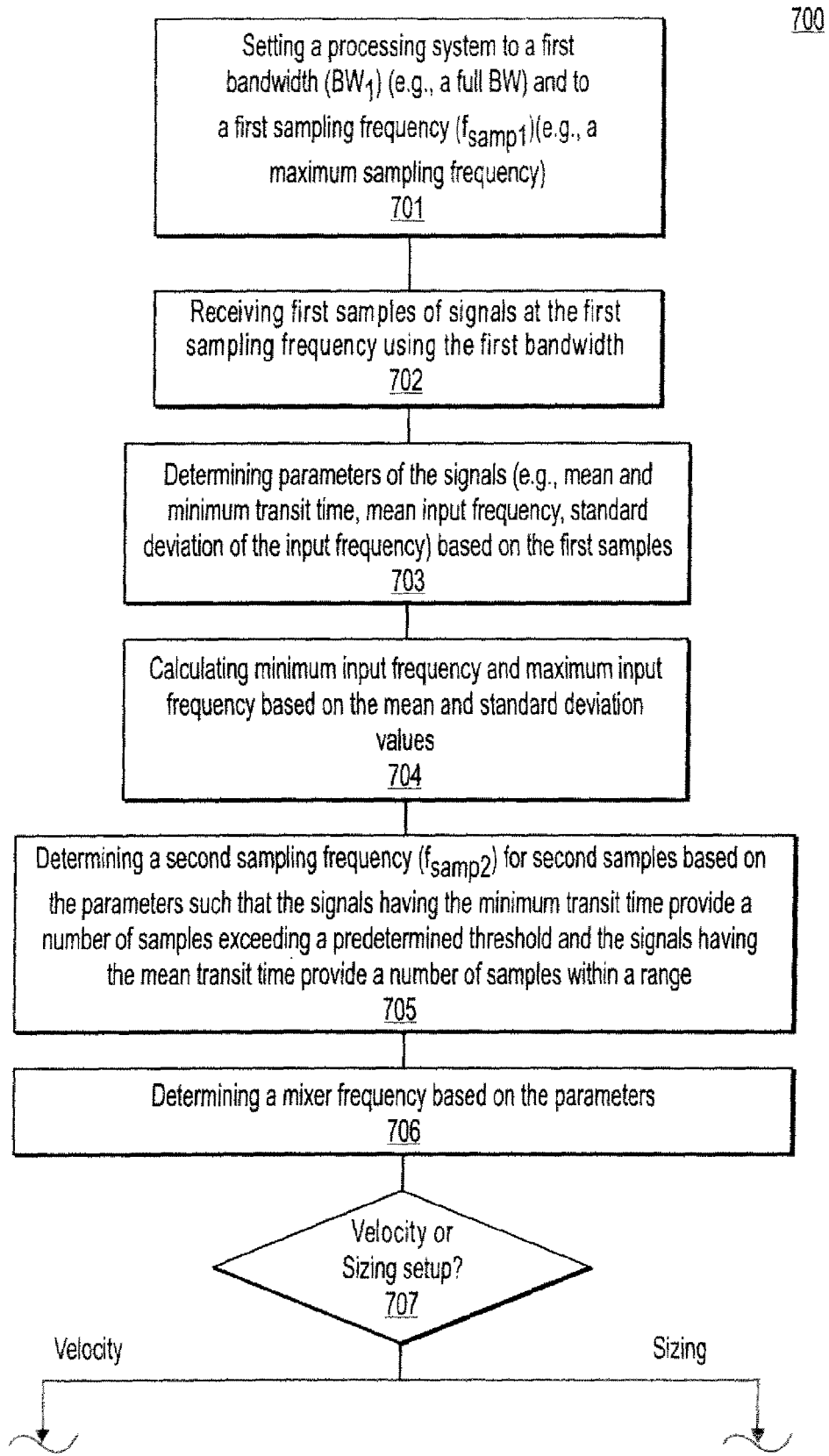
FIG. 7 is a flowchart of one embodiment of a method to automatically set up a signal processing system to determine the sizes and velocities of the spherical objects.
Figure 7:
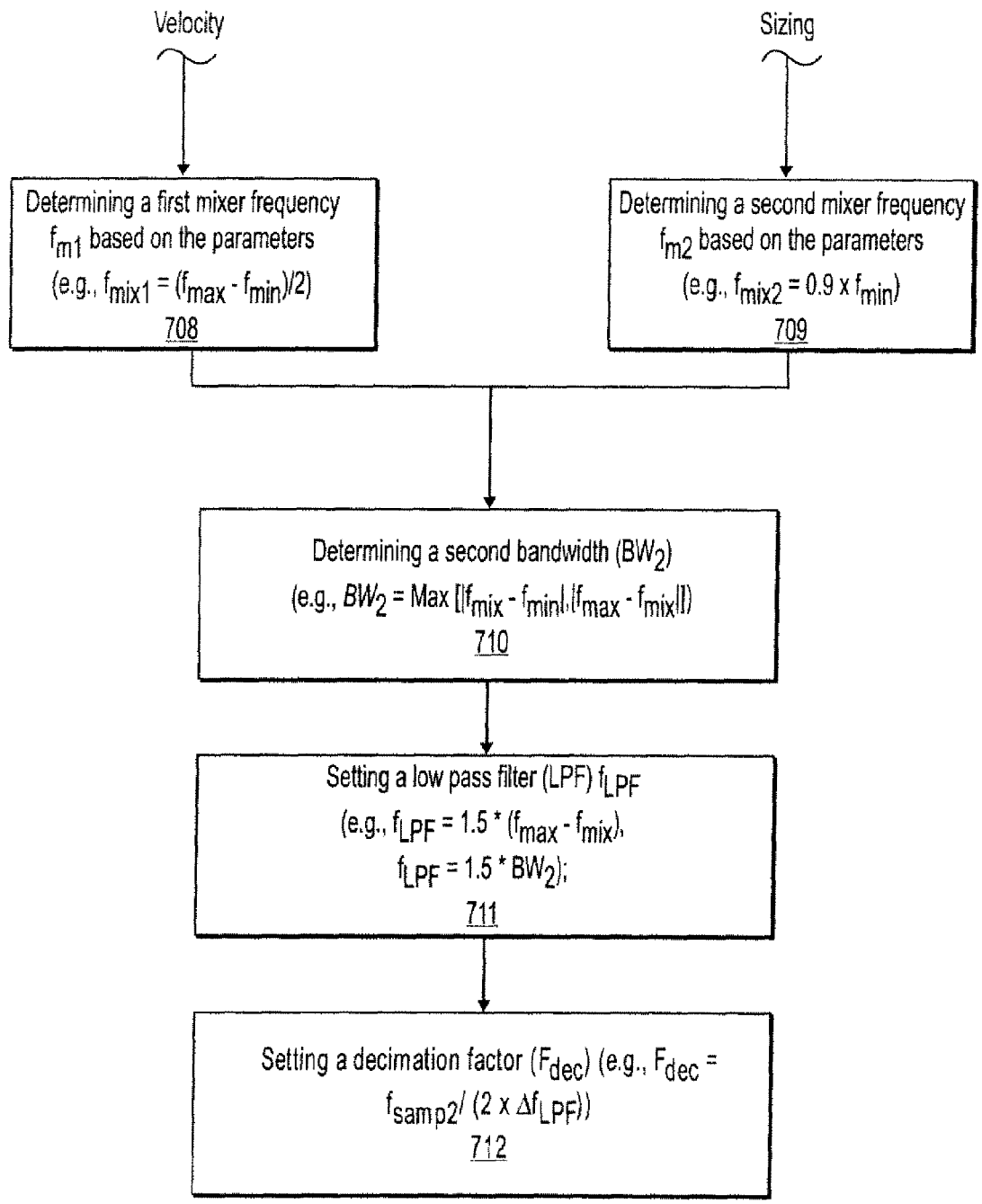
Figure 8:
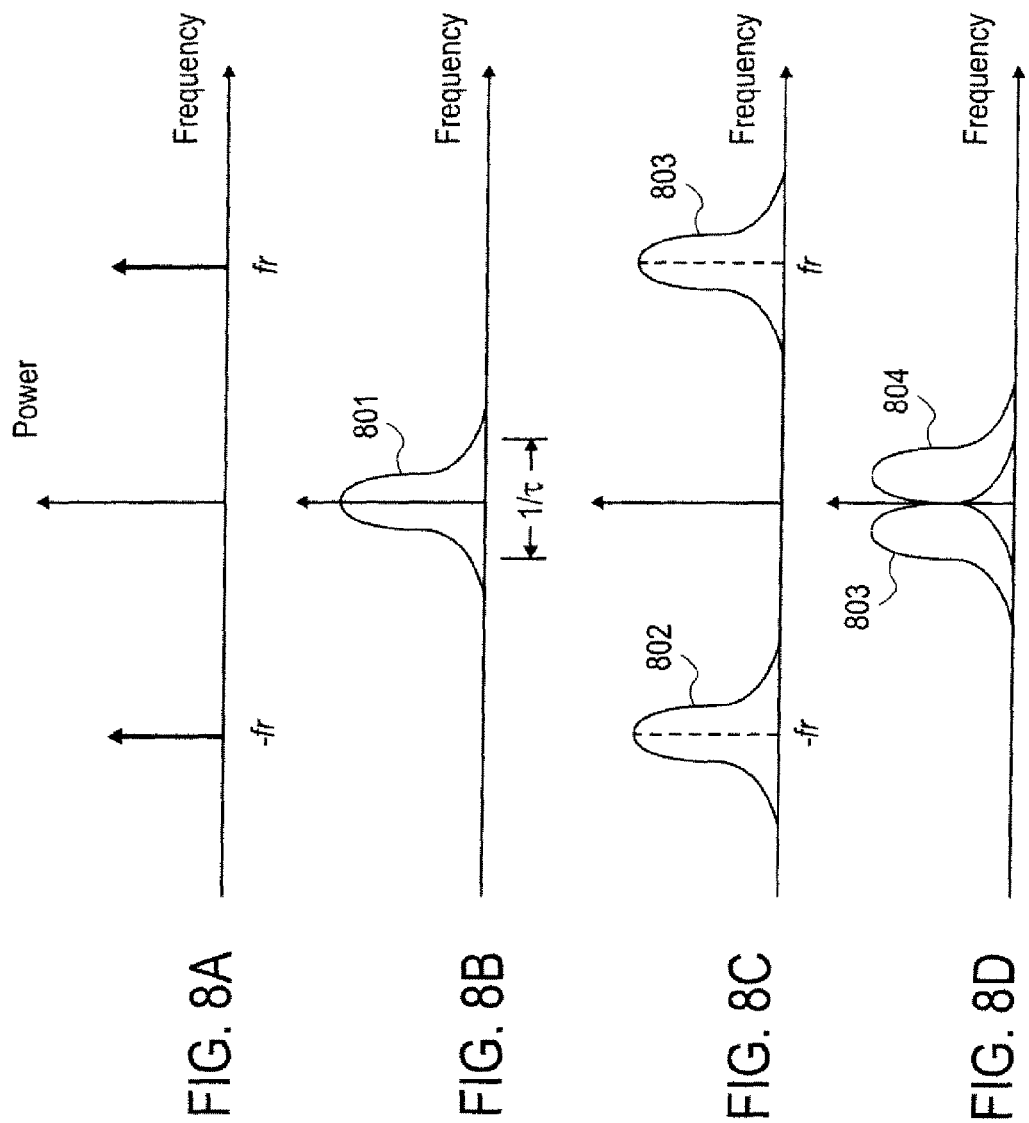
FIGS. 8A-8D illustrate embodiments of spectrums of electrical signals.

FIG. 7 is a flowchart of one embodiment of a method to automatically set up a signal processing system to determine the sizes and velocities of the spherical objects. Method begins with operation 701 that involves setting the signal processing system to a first bandwidth ("BW$_1$") and to a first sampling frequency. For one embodiment, the BW$_1$ is a full (e.g., maximum) bandwidth of the signal processing system. For one embodiment, a first sampling frequency ($f_{samp1}$) is the maximum sampling frequency of the signal processing system. Operation 701 may be performed in response to receiving of a user request. Method continues with operation 702 that involves receiving first samples of signals at the first sampling frequency using the first bandwidth. A number of the first samples may be, for example, between about 100 samples to about 1000 samples. Next, the first parameters of the signals are determined based on the first samples at operation 703. For one embodiment, the first parameters, for example, mean and minimum transit time, mean value of input frequency measurements, and standard deviation of the input frequency measurements are computed based on the first samples. Further, at operation 704 a minimum input frequency and a maximum input frequency of the signals are calculated based on the mean and standard deviation values. For one embodiment, the maximum input frequency is calculated by adding 3 times the standard deviation to the mean value of the input frequency measurements. The minimum input frequency is calculated by subtracting 3 times the standard deviation from the mean value of the input frequency measurements. Next, operation 705 is performed that involves determining of a second sampling frequency ($f_{samp2}$) based on the first parameters. For one embodiment, the second sampling frequency is determined for a digital section of the signal processing system illustrated in FIGS. 3 and 6 to sample second samples. The second sampling frequency is determined such that the signals having the minimum transit time provide a number of samples exceeding a predetermined threshold and the signals having the mean transit time provide a number of samples within a range. For example, the second sampling frequency is selected such to ensure that each of the burst signals having the minimum transit time can provide more than about 32 samples. For example, the second sampling frequency is selected such to ensure that each of the burst signals having the mean transit time can provide from about 128 to about 256 samples. A number of the second samples to provide a single measurement point may be, for example, between about 100 samples to about 1,000 samples. The second samples are used to refine the sampling frequency to better define the transit time. Next, at operation 706, a mixer frequency is determined based on the first parameters. For one embodiment, the mixer frequency of the one or more mixers of the analog section of the signal processing system, as described in FIGS. 3 and 6 is set based on the first samples. For one embodiment, the mixer frequency is set based on the minimum input frequency and maximum input frequency. At operation 707 determination is made if velocity set-up, e.g., a LDV set-up, or sizing setup, e.g., a PDI set-up, is performed. For one embodiment, at operation 708, if the velocity set up is performed, the mixer frequency is set to the average of the estimated maximum input frequency f and minimum input frequency $f_{min}$. For one embodiment, the mixer frequency $f_{mix1}$ is set to $f_{mix1}=(f_{max}-f_{min})/2$. For one embodiment, at operation 709, if the sizing set-up is performed, the mixer frequency is set to 0.9 times the estimated minimum frequency. For some PDI applications, the computed mixer frequency is less than the signal bandwidth (estimated by subtracting the estimated maximum frequency from the estimated minimum frequency). For these cases, the mixer frequency is set to 1.1 times of the maximum input frequency. Next, a signal bandwidth (BW$_2$) is determined at operation 710. For one embodiment, the BW$_2$ is set as follows.

$$BW_2 = \text{Max}[|f_{mix}-f_{min}|, |f_{max}-f_{mix}|] \quad (5)$$

Next, at operation 711 a low pass filter is set based on the mixer frequency. For one embodiment, one or more low pass filters of the analog section of the signal processing system as described in FIGS. 3 and 6 are set based on the mixer frequency. For one embodiment, the low pass filter cut-off frequency $f_{LPF}$ is set as follows:

$$f_{LPF} = 1.5*(f_{max}-f_{mix}) \quad (6)$$

For another embodiment, the low pass filter bandwidth $\Delta f_{LPF}$ is set as follows:

$$\Delta f_{LPF} = 1.5*BW_2 \quad (7)$$

Next, at operation 712 a decimation factor $F_{dec}$ is set based on the low pass filter. The decimation factor is used to ensure that the sampled data are sampled at the digital domain burst detector at twice of the processor bandwidth, as described above with respect to FIGS. 3 and 6. For an embodiment, the processor bandwidth is equal to $\Delta f_{LPF}$.

For one embodiment, the decimation factor is computed as follows:

$$F_{dec} = f_{samp2}/(2 \times \Delta f_{LPF}) \quad (8)$$

For one embodiment, operations 701-711 are continuously repeated to refine the selection of the signal processor parameters. For one embodiment, the signal processor parameters are a mixer frequency, a low pass filter setting, a sampling frequency, or any combination thereof.

For PDI applications, phase measurements may not be accurate when the signal frequency is close to the mixer frequency. This is especially true for real signals (e.g., if the imaginary part Si(t) is about zero).

FIGS. 8A-8D illustrate an embodiment of signal spectra. FIG. 8A illustrates a spectrum of a continuous sinusoidal signal with a frequency fr. As shown in 8A, the spectrum has two frequency components (i.e. positive fr and negative −fr components). The spectrum having the Gaussian envelope 801 is shown in FIG. 5b. As shown in FIG. 8B, the width 1/τ of Gaussian envelope 801 is determined by a signal transit timer. A spectrum of a Doppler Gaussian envelope signal is shown in FIG. 8C. As shown in FIG. 8C, fr>>1/τ and signal components 802 and 803 do not interact, and the phase of the signal can be measured accurately at fr. A spectrum of another Doppler Gaussian envelope signal is shown in FIG. 8D. As shown in FIG. 8D, fr<1/τ and the interaction between the two components 803 and 804 may lead to inaccuracy in the phase measurement. To avoid the measurement inaccuracies, the mixer frequency is selected so that the mixer output has at least 2 cycles within the burst signal. This can be achieved by setting the mixer frequency as follows:

$$(f_i - f_{mix}) \times \tau_i \geq M \quad (9)$$

where, $f_{mix}$ is the mixer frequency, $f_i$ is the signal frequency of the signal i, $\tau_i$, is the transit time of the burst signal i, and M is the minimum number of cycles of the signal used for phase measurement.

For one embodiment, the low pass filter with a cut-off frequency $f_{LPF}$ is then selected as follows:

$$|f_{min} - f_{mix}| < f_{LPF} \quad (10)$$

$$|f_{max} - f_{mix}| < f_{LPF} \quad (11)$$

$$|f_{min} + f_{mix}| > f_{LPF} \quad (12)$$

$$|f_{max} + f_{mix}| > f_{LPF} \quad (13)$$

As described above, the sampling frequency is selected to ensure at least a minimum number of samples for the shortest duration signal bursts. On the other hand to ensure reliable signal detection in the presence of noise, the sampling frequency should not be larger than twice the low pass filter $f_{LPF}$. To accommodate for these two independent conditions, a decimation feature is used. For an embodiment, the signal sampling frequency is determined by the minimum transit time, as described above. The signal sampling frequency is then decimated by a variable factor (e.g., any number from about 1 to about 8) to insure reliable signal detection.

Figure 9:
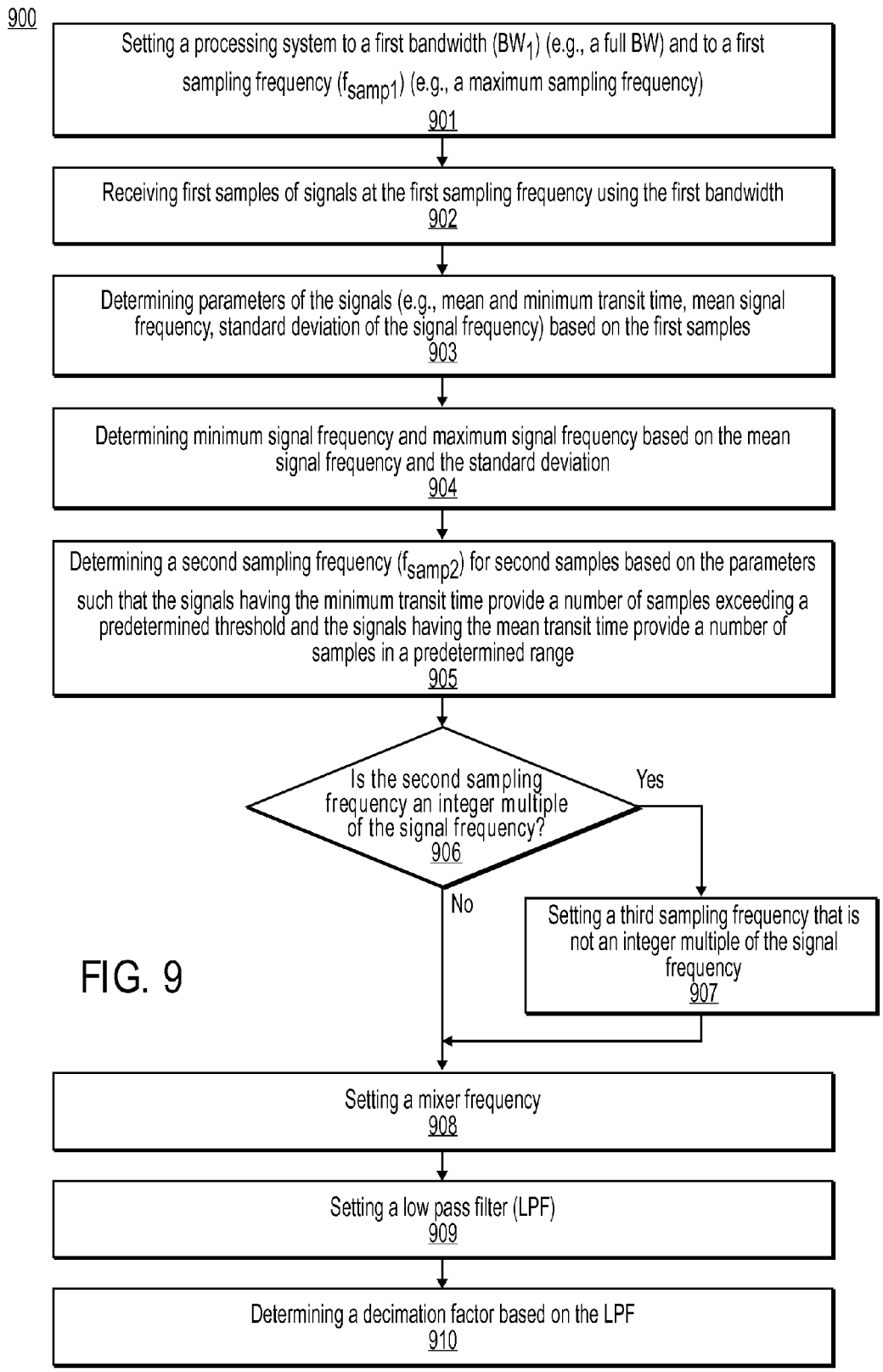
FIG. 9 shows a flowchart of another embodiment of a method to automatically set up a signal processing system to determine the sizes and velocities of the spherical objects.

FIG. 9 shows a flowchart of another embodiment of a method to automatically set up a signal processing system to determine the sizes and velocities of the spherical objects. Method begins with operation 901 that involves setting the signal processing system to a first bandwidth ("BW₁") and to a first sampling frequency. For one embodiment, the BW₁ is a full (e.g., maximum) bandwidth of the signal processing system. For one embodiment, a first sampling frequency ($f_{samp1}$) is the maximum sampling frequency of the signal processing system. Method continues with operation 902 that involves receiving first samples of signals at the first sampling frequency using the first bandwidth. Next, the first parameters of the signals are determined based on the first samples at operation 903. For one embodiment, the first parameters, for example, mean and minimum transit time, mean value of input frequency measurements, and standard deviation of the input frequency measurements are computed based on the first samples. Further, at operation 904 a minimum input frequency and a maximum input frequency of the signals are calculated based on the mean and standard deviation values. For one embodiment, the maximum input frequency is calculated by adding 3 times the standard deviation to the mean value of the input frequency measurements. The minimum input frequency is calculated by subtracting 3 times the standard deviation from the mean value of the input frequency measurements. Next, operation 905 is performed that involves determining of a second sampling frequency ($f_{samp2}$) based on the first parameters. For one embodiment, the second sampling frequency is determined for a digital section of the signal processing system illustrated in FIGS. 3 and 6 to sample second samples. The second sampling frequency is determined such that the signals having the minimum transit time provide a number of samples exceeding a predetermined threshold and the signals having the mean transit time provide a number of samples within a range. For example, the second sampling frequency is selected such as to ensure that the burst signals having the minimum transit time can provide more than about 32 samples. For example, the second sampling frequency is selected such to ensure that the burst signals having the mean transit time can provide from about 128 to about 256 samples. Next, a determination is made at operation 906 whether the second sampling frequency is an integer multiple of the signal frequency. If the second sampling frequency is an integer multiple of the signal frequency, at operation 907 a third sampling frequency is set that is not an integer multiple of the signal frequency. If the second sampling frequency is not an integer multiple of the signal frequency, the method 900 continues with operation 908. Operation 908 involves setting a mixer frequency based on the first parameters, as described above with respect to FIG. 7. Method 900 continues with operation 909 that involves setting a low pass filter based on the mixer frequency, as described above with respect to FIG. 7. Next, at operation 910 a decimation factor is determined based on the LPF setting, as described above with respect to FIG. 7.

For an embodiment, method 900 is used to resolve ambiguity in phase measurements that occurs when the sampling frequency is an integer multiple of the signal frequency.

Figure 10:
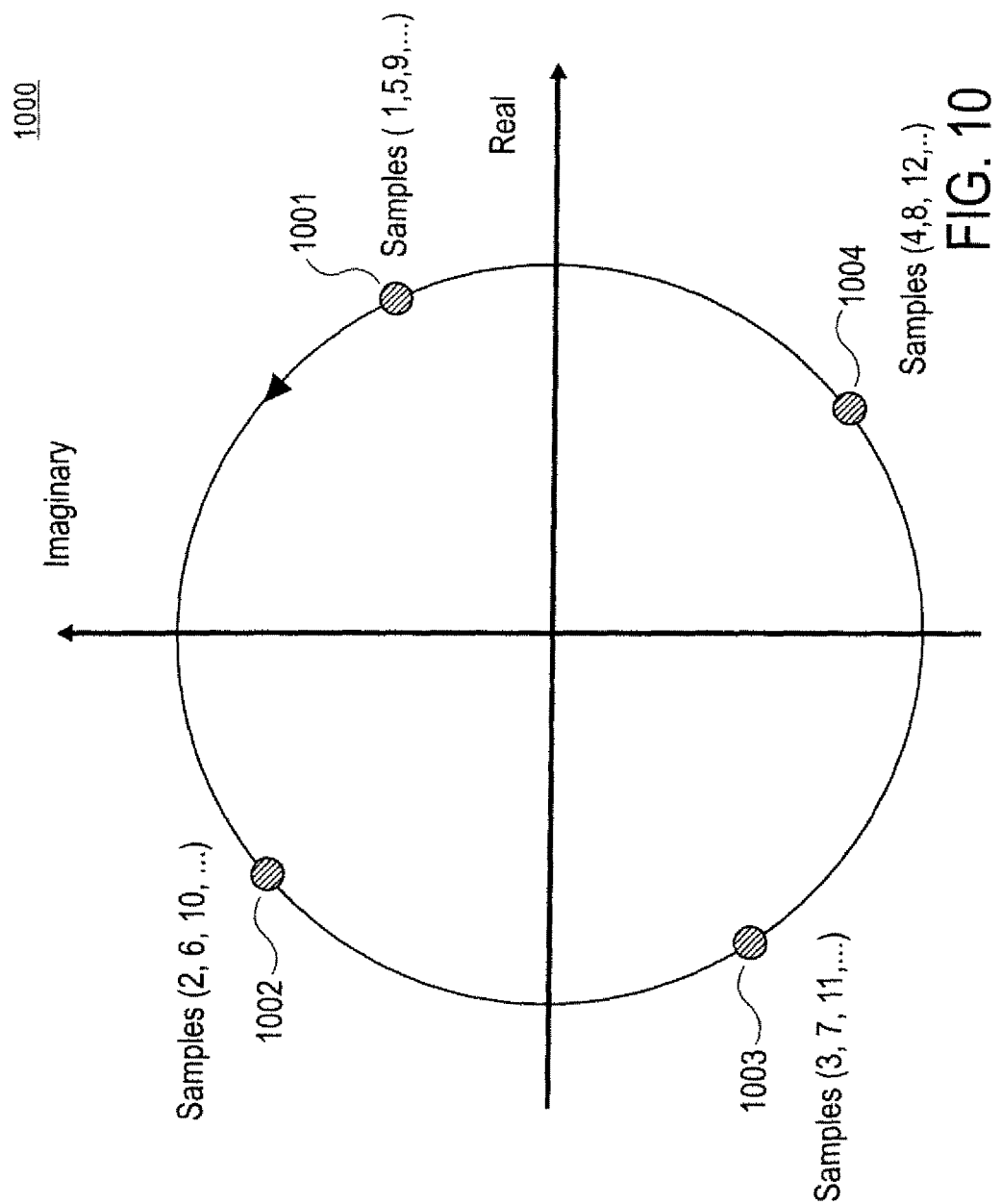
FIG. 10 illustrates one embodiment of a complex signal data in the absence of noise when the sampling frequency is four times of the input signal.

FIG. 10 illustrates one embodiment of complex signal data in the absence of noise when the sampling frequency is four times the input signal. As shown in FIG. 10, sampled data 1001-1004 repeats itself after the fourth sample and the phase measurement accuracy may not improve by increasing the number of samples over 4. For this case, the phase measurement accuracy may be determined by the digitization noise. For N-bit Analog-to-Digital converter ("ADC"), the phase measurement ambiguity $\Delta\theta$ can be determined as follows:

$$\Delta\theta = \sin^{-1}(\frac{1}{2}^N) \quad (14)$$

For PDI Applications.

Using the adaptive sampling techniques where the signal is sampled at different rates overcomes the ambiguity in phase measurements and provides a phase measurement accuracy at least better than 2 degrees. The sampling frequencies are selected such that if one of the sampling frequencies is a multiple integer of the signal frequency, another sampling frequency that is not a multiple integer of the signal frequency is selected. For one embodiment, the frequency of the incoming signals can be measured using any of these sampling frequencies, and the phase of the incoming signals is measured using only the data sampled at a rate that is not a multiple integer of the signal frequency.

Figure 11:
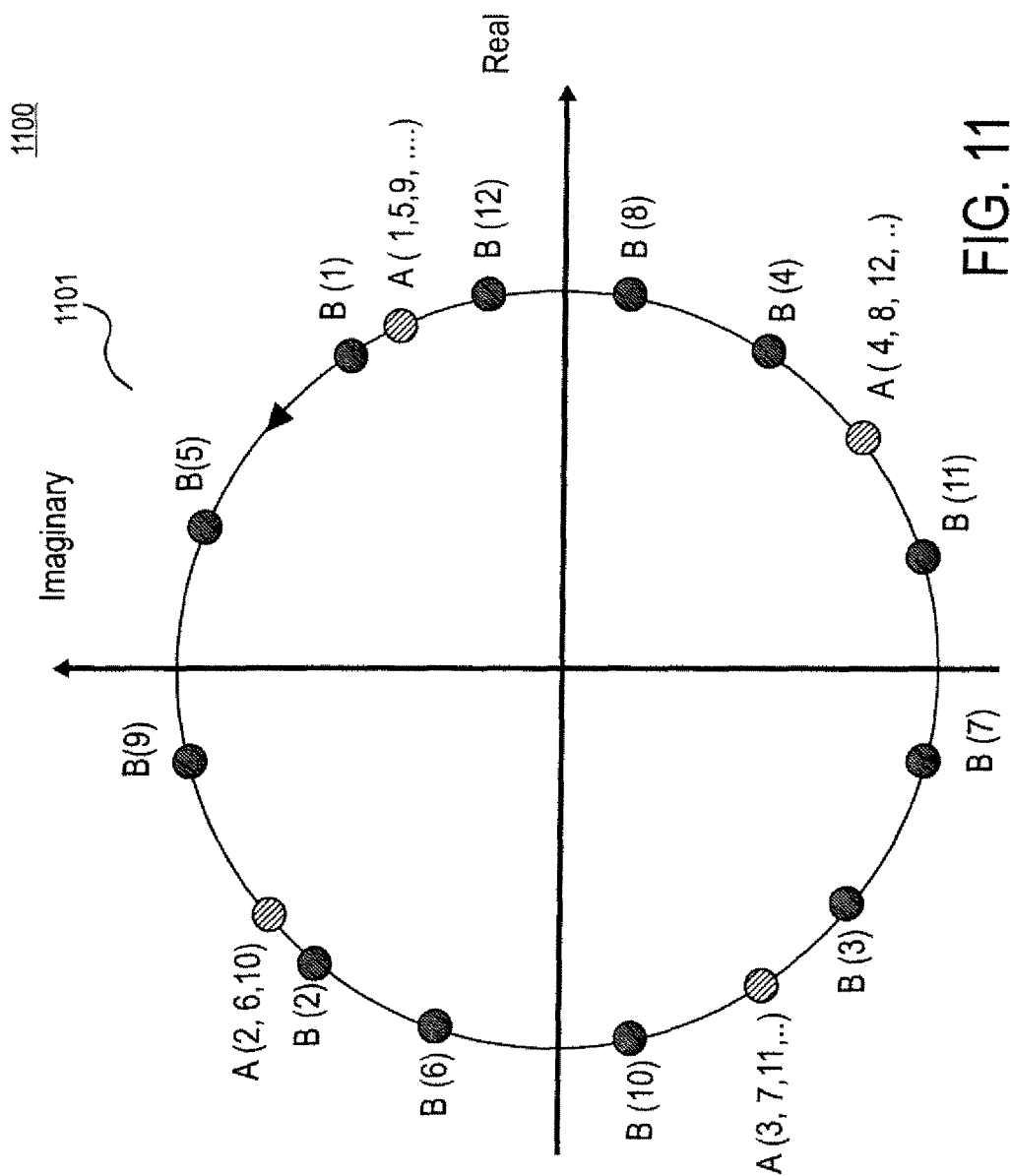
FIG. 11 shows the signal sampled data using two sampling frequencies according to one embodiment of the invention.

FIG. 11 shows the signal sampled data using two sampling frequencies according to one embodiment of the invention. The sampled data A are obtained with the first sampling frequency that is four times the signal frequency. The sampled data B are obtained with a second frequency that is higher than the first sampling frequency. As shown in FIG. 11, when samples A do not effectively span complex plain 1101, samples B effectively span complex plain 1101.

Figure 12:
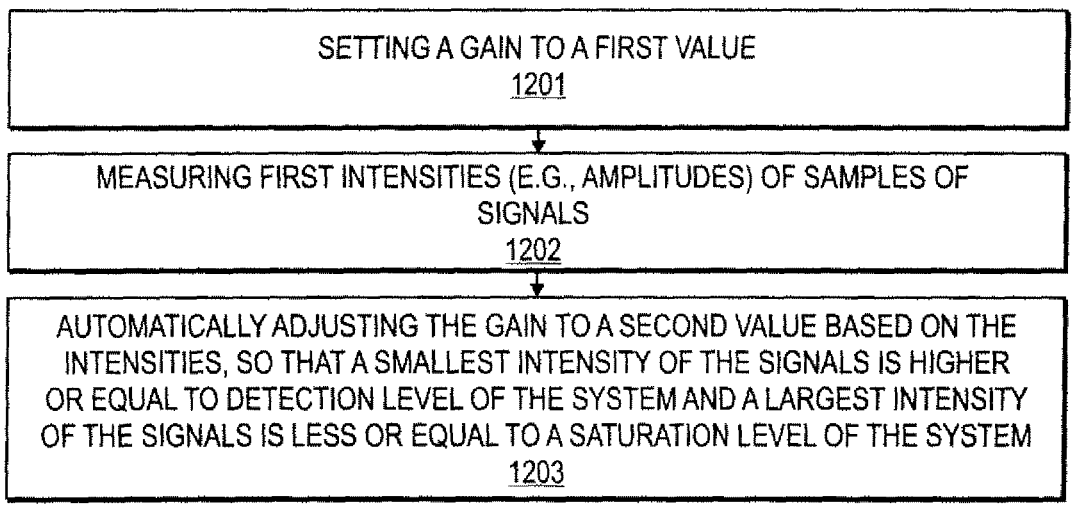
FIG. 12 is a flowchart of another embodiment of a method to automatically set up a signal processing system to determine the sizes and velocities of the spherical objects that includes automatically adjusting a gain.

FIG. 12 is a flowchart of another embodiment of a method to automatically set up a signal processing system to determine the sizes and velocities of the spherical objects that includes automatically adjusting a gain. An analog front-end gain of the photodetector section of the signal processing system may vary over the range of 100 to more than 10000 depending on the strength of the optical signals. The gain of the signal processing system can be adjusted to accommodate a wide range of the amplitudes of the incoming signals. The amplitude range of the incoming signals may vary, for example, over the range of 1:10000. Method 1200 begins with operation 1201 that involves setting a gain of the signal processing system to a first value e.g., an intermediate value. For one embodiment, the gain of the signal processing system is an analog front-end gain of the photodetector section of the signal processing system described above with respect to FIGS. 3 and 6. Method 1200 continues with operation 1202 that involves measuring intensities of the first samples. For one embodiment, the intensities (or amplitudes) of the incoming optical signals from a spherical object are measured. For one embodiment, the first samples to measure the intensities are sampled with a first sampling frequency, e.g., a maximum sampling frequency and at a full bandwidth of the signal processing system, or any other sampling frequency. Next, at operation 1203, the gain is automatically adjusted to a second value based on the measured intensities (or amplitudes), so that a smallest intensity of the incoming signals is higher or equal to a minimum detection level of the system and a largest intensity of the incoming signals is less or equal to a saturation level of the system. For one embodiment, a histogram is generated based on the measured intensity or amplitude of the incoming optical signals. The histogram is then used to determine the optimum system front-end gain. For one embodiment, the gain is adjusted by adjusting the High Voltage (HV) of the photodetectors (e.g., PMTs) used in the photodetector section of the signal processing system. For one embodiment, HV is adjusted automatically by using the gain-HV dependencies supplied by a photodetector manufacture, to ensure that all the signals fall between the system minimum detection level and the saturation level. For another embodiment, the gain is adjusted to the second value by attenuating optical signals in front of a photodetector, using, for example, a variable optical attenuator.

For another embodiment, dependencies of the sampled signal amplitude from the measured drop size may be used to adjust the gain of the signal processing system.

For one embodiment, the amplitude of the signal for a selected number of signals is measured and compared to the optimum signal amplitude. The spherical objects typically scatter light in proportion to their diameter squared. For example, for a size range from about 50 to about 1, the signal amplitude range may vary from about 2500 to about 1. In order to be able to detect and measure the smallest particles without exceeding the amplitude limits for the large particles, the gain of the photodetectors (e.g., PMTs) is adjusted. Because the size range of the spherical objects may vary from point-to-point within the spray or particle field, the adjustment of the gain is performed rapidly and repeatedly to provide an appropriate photodetector gain setting for each measurement location. For one embodiment, the gain of the photodetectors is adjusted to fit peak amplitudes of the incoming signals to a parabolic theoretical signal amplitude curve for each particle size class. Each of the particle size class has a range of signal amplitudes. For an embodiment, an automatic photodetector gain adjustment at each measurement location serves to accommodate any laser beam attenuation, scattered light attenuation, change in the drop size distribution, and window contamination.

The automatic gain adjustment allows automatic traversing of the spray pattern without user intervention. At each measurement location, the gain is automatically adjusted to measure the spray or particle field having different characteristics. By automating the signal processing system setup, the entire traversing and data acquisition process can be fully automated so that system can perform multitude of measurements without the need for an instrument user to be present to make the changes and adjustments at each measurement location.

Figure 13:
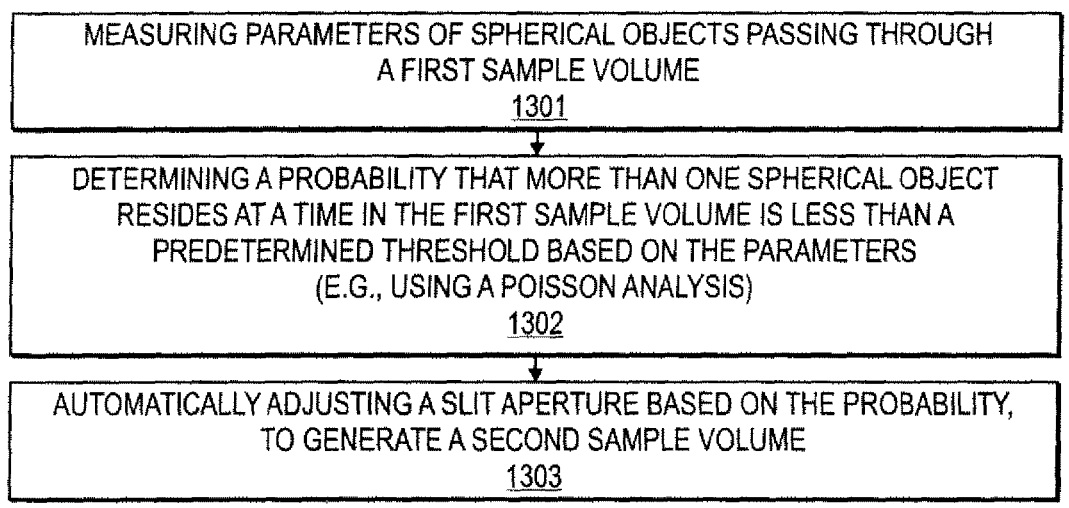
FIG. 13 is a flowchart of one embodiment of a method to automatically set up a signal processing system to determine the sizes and velocities of the spherical objects that includes automatically adjusting an aperture of the signal processing system.

FIG. 13 is a flowchart of one embodiment of a method to automatically set up a signal processing system to determine the sizes and velocities of the spherical objects that includes automatically adjusting an aperture of the signal processing system. The aperture of the signal processing system is adjusted to accommodate current density of the spherical objects. Method begins with operation 1301 that involves measuring parameters of spherical objects passing through a first sample volume. For one embodiment, the parameters of the spherical objects include the arrival rate of the spherical objects passing through the sample volume. For one embodiment, a mean arrival rate of the spherical objects passing through the sample volume is measured. For one embodiment, the arrival rate can be calculated based on the time of arrival of the spherical object to the sample volume. For another embodiment, the parameters of the spherical objects include the distance between the spherical objects passing through the sample volume. For one embodiment, the distance between the spherical objects passing through the sample volume includes an inter-arrival time between the spherical objects. For another embodiment, a mean distance between the spherical objects passing through the sample volume is measured. For another embodiment, the distance between the spherical object passing through the sample volume is calculated based on the velocity of the spherical objects and arrival time of the spherical objects.

Method continues with operation 1302 that involves determining a probability that more than one spherical object resides at a time in the first sample volume is less than a predetermined threshold based on the measured parameters. For one embodiment, the predetermined threshold is defined as is a preset percentage, e.g., about 20%. For one embodiment, the probability that more than one spherical object resides at a time in the first sample volume is determined by applying probability analysis, e.g. a Poisson statistics. The probability analysis is applied to select the optimum sample volume size to limit coincidence error and maximize data rates. For one embodiment, an alert signal is automatically issued when an optics of the signal processing system needs to be changed. Next, the operation 1303 is performed that involves automatically adjusting the aperture of the signal processing system based on the probability to provide a second sample volume. For one embodiment, the aperture of the signal processing system includes a movable strip-like slit aperture positioned in front of the photodetector section of the signal processing system, as described above with respect to FIG. 2. For an embodiment, an adjustable aperture having a round or rectangular shape, or any other aperture that is known to one of ordinary skill in the art of optics manufacturing is used.

Typically, single particle counter-based measurements to determine the sizes and velocities of the spherical objects require a substantially high probability, for example more than about 90% that only one particle exists in the measurement volume (sample volume) at one time. This requirement may be analyzed using a probability analysis, e.g., Poisson statistics. Larger the density of the spherical objects, smaller sample volume is required to ensure that this condition is met. For example, in dense sprays, a substantially small volume is required. When the density of the spray or particle field is low, a larger sample volume may be required to maintain an adequate data rate. For one embodiment, in sprays where the number density of the spray is very low at the edges and increases to a relatively high number density at the center of the spray, the sample volume is adjusted as described above to accommodate each location to optimize the data acquisition. As such, an automatic selection and recording of the aperture limits coincidence errors. The probability analysis approach assures that a statistically significant number of samples, e.g. at least 1000 samples, are acquired for each location in the spray field. By adjusting the sample volume size for each measurement location based on the probability analysis, the substantially high data acquisition rate is maintained while the loss of data due to coincidence errors is minimized. A coincidence error may occur when more than one spherical object occupies the sample volume. Further, using the probability analysis to adjust the sample volume ensures that data are not lost because of signal rejections when more than one spherical object occupies the sample volume.

Figure 14:
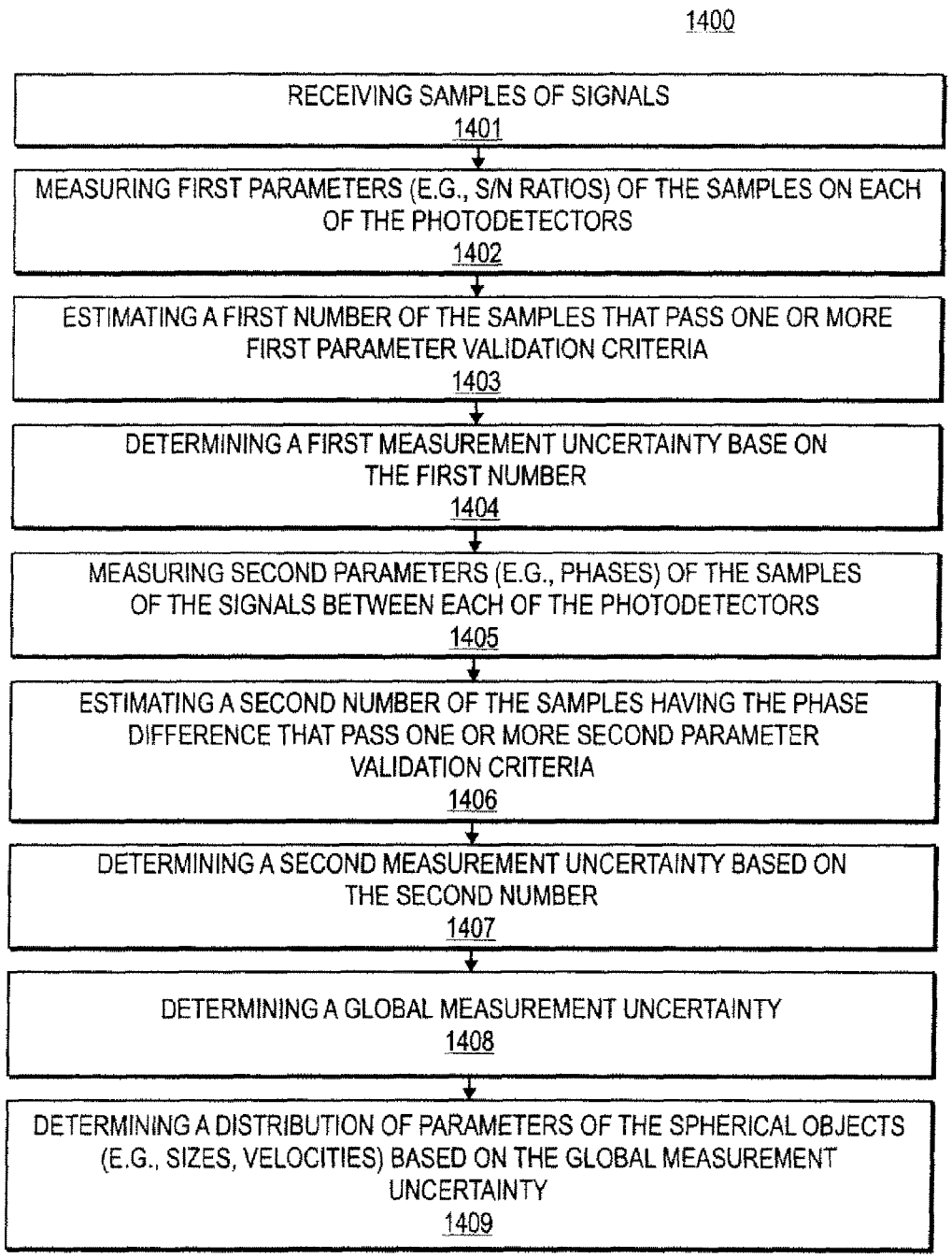
FIG. 14 is a flowchart of one embodiment of a method to automatically set up a signal processing system to determine the sizes and velocities of the spherical objects that includes automatically estimating a measurement uncertainty of the signal processing system for each of the measured spherical objects.
Figure 15:
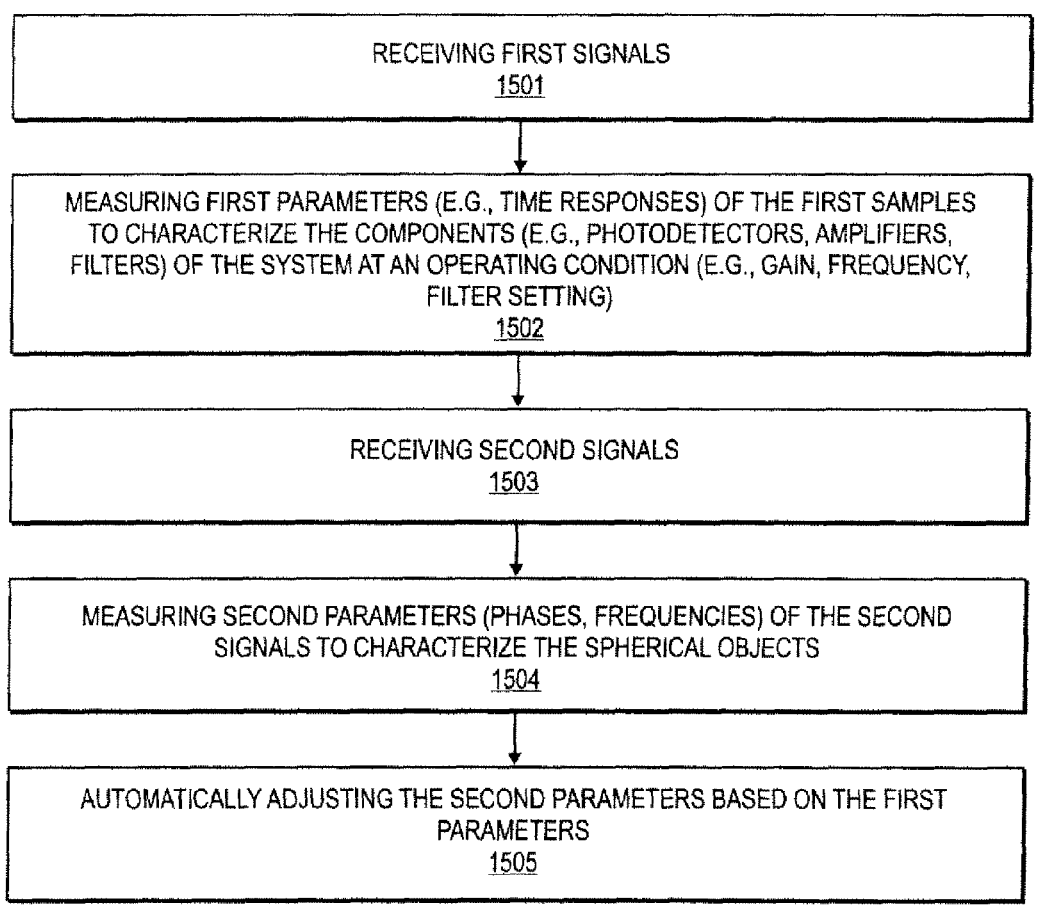
FIG. 15 is a flowchart of one embodiment of a method to automatically set up a signal processing system to determine the sizes and velocities of the spherical objects that includes an automated detector calibration.

FIG. 14 is a flowchart of one embodiment of a method to automatically set up a signal processing system to determine the sizes and velocities of the spherical objects that includes automatically estimating a measurement uncertainty of the signal processing system for each of the measured spherical objects. Method 1400 begins with operation 1401 that involves receiving samples of signals from a signal source. Method continues with operation 1402 of measuring first parameters of the samples on photodetectors. The first parameters include measuring a signal-to-noise ratio of the samples of each of the signals on each of the photodetectors. Next, estimating a first relative number of the samples that pass one or more first parameter validation criteria are performed at operation 1403. For example, the relative number of the samples that have S/N ratios that exceed a predetermined threshold >50%, are estimated. The S/N ratio for each of the photodetector outputs is computed by computing the power spectrum of the signal using the Discreet Fourier Transform ("DFT"). The signal power is then computed by computing the power of the DFT bin (bins) with maximum power. The S/N ratio is then computed by dividing the signal power by the sum of the power of the remaining DFT bins. The S/N ratio can be set to any value between 0 dB to 10 dB depending on the level of measurement uncertainty. For one embodiment, the relative number of the samples that pass one or more first parameter validation criteria are estimated using statistical methods. Method continues with operation 1404 that includes determining a first measurement uncertainty based on the estimated first relative number of the samples. For one embodiment, the first measurement uncertainty is estimated quantitatively based on the first number. Next, second parameters of the samples of the signals are measured at operation 1405. For one embodiment, the second parameters include phase differences of the samples of the signals between each of the photodetectors. For one embodiment, the second parameters include comparison of measurements of the phase difference between photodetector signals using different sections of the signals. For example, the photodetector signals are divided into a first half and a second half. The phase difference is then measured for the first half and the second half. These two measurements should agree within a few degrees, e.g., within about 10 degrees. For one embodiment, the phase comparison for each of the three pairs of detectors is performed. For one embodiment, each of the signals is evaluated in sections over the duration of the signal to determine the phase. For another embodiment, the second parameters include frequencies of the samples of the incoming signals. For one embodiment, the signal is divided into several sections (e.g., a first half and a second half). The frequencies of these sections should agree within a few KHz, e.g., about 10 KHz. At operation 1406 estimating a second relative number of the samples that pass one or more second parameter validation criteria is performed. For example, the relative number of the samples that have the second parameters (e.g., phase differences, frequency differences, or a combination thereof) that exceed a predetermined threshold >50%, are estimated. For one embodiment, the relative number of the samples that pass one or more second parameter validation criteria are estimated using statistical methods.

Next, a second measurement uncertainty is determined based on the second number at operation 1407. For one embodiment, the second measurement uncertainty is estimated quantitatively based on the first number. Further, method 1400 continues with operation 1408 that includes determining a global measurement uncertainty. For one embodiment, the global measurement uncertainty is determined based on the first measurement uncertainty and the second measurement uncertainty. For one embodiment, each of a first measurement uncertainty and the second measurement uncertainty is determined after measuring both the first parameters and second parameters. For another embodiment, the global measurement uncertainty is determined based on the first relative number and the second relative number. For one embodiment, a plurality of parameter measurement uncertainties is quantitatively estimated for each of the parameters of the signals, and then the global measurement uncertainty is quantitatively estimated based on each of the parameter measurement uncertainties. Next, method 1400 continues with operation 1409 that includes determining a distribution of parameters of the spherical objects using the global measurement uncertainty. The uncertainty for each of the measured spherical object can be incorporated into the calculation of the mean values for the measured size and velocity distributions. For one embodiment, the measurement data are acquired until a user-defined uncertainty band has been reached. For one embodiment, the parameters of the spherical objects include sizes of the spherical objects, velocities of the spherical objects, or a combination thereof. For one embodiment, the validation information (e.g., validation criteria) are stored in a memory of the processing system with each data set. For one embodiment, validation criteria are developed to estimate the measurement uncertainty at each measurement location.

FIG. 15 is a flowchart of one embodiment of a method to automatically set up a signal processing system to determine the sizes and velocities of the spherical objects that includes an automated detector calibration. Method begins with operation 1501 that involves receiving first signals to characterize the components of the signal processing system. For one embodiment, the first signals to characterize the components are sent to the signal processing system from a calibration source, e.g., a built-in laser diode. The components of the signal processing system are for example, cables, photodetectors, pre-amplifiers, amplifiers, and filters, and any other active and passive components that may have varying time response. Method continues with operation 1502 that involves measuring first parameters of the first signals to characterize the components of the system at an operating condition. For one embodiment, the first parameters of the first signals to characterize the components of the system are measured automatically in response to changing of the operating condition. For one embodiment, the first parameters are, for example, time responses, time delays, and phase shifts that characterize the components. For one embodiment, the operating condition of the signal processing system is a gain setting, an operating frequency, a filter setting, other system setting, or any combination thereof. For one embodiment, the measuring of the first parameters includes setting a shutter coupled to the photodetector section of the system "ON" to avoid scattered light. For one embodiment, a look up table based on the measurements from the calibration diode is automatically generated based on the measured first parameters. The look up table includes measured first parameters (e.g., time responses, time delays, and phase shifts) at each of a plurality of operating conditions. For one embodiment, the look up table is automatically generated periodically to follow a current operating (measurement) condition. For one embodiment, the look-up table is automatically generated at each new operating condition. For one embodiment, the look-up table is automatically generated when one or more operating conditions change. For one embodiment, the look up table that includes measured first parameters at each of the plurality of operating conditions is stored in a memory of the system to measure the size and velocity of spherical objects.

Next, at operation 1503 second signals are received. For one embodiment, second signals are received from a spherical object passing through a sample volume. Next, operation 1504 is performed that involves measuring second parameters of the second signals to characterize spherical objects. For one embodiment, the second parameters to characterize the spherical objects are e.g., phases, frequencies, and amplitudes of the second signals. For one embodiment, the measuring of the second parameters includes setting a shutter coupled to the photodetector section of the system "OFF" to receive the optical signals from the spherical objects. Further, operation 1505 is performed that involves automatically adjusting the second parameters based on the first parameters. For one embodiment, the second parameters are adjusted by subtracting the first parameters from the second parameters. For one embodiment, the second parameters are automatically adjusted based on the look-up table stored in the memory. That is, the second parameters can be automatically adjusted when one or more operating conditions change. For another embodiment, moving to another measurement location is performed, and operations 1501-1505 are repeated at another measurement location to calibrate the system. As such, method 1500 is used to calibrate the signal processing system at each location to measure the size and velocity of the spherical objects. Method 1500 accounts for all possible phase delays in the components of the system before measuring the size and velocity of the spherical particles. The system to measure the size and velocity of the spherical objects is calibrated using the method 1500 at the full range of frequencies for set up. For one embodiment, the system automatically steps through the operating frequencies at the set-up conditions and tabulates the phase shifts. For one embodiment, first signals and the second signals are in the approximate range of 20 MHz to 100 MHz. For one embodiment, time delays of the signals are in the approximate range of 0.1-100 nsec. Method 1500 performs calibration automatically and covers parameters of all components of the system. This calibration procedure is fully automated and invisible to the system user that simplifies the operation of the system and ensures reliable measurements.

In practice, methods described with respect to FIGS. 7, 9, and 12-15 may constitute one or more programs made up of machine-executable instructions. Describing the methods with reference to the flowcharts in FIGS. 7, 9, and 12-15 enables one skilled in the art to develop such programs, including such instructions to carry out the operations (acts) represented by logical blocks of the flowcharts depicted in FIGS. 7, 9, and 12-15 on suitably configured machines (the processor of the machine executing the instructions from machine-readable media). The machine-executable instructions may be written in a computer programming language or may be embodied in firmware logic or in hardware circuitry. If written in a programming language conforming to a recognized standard, such instructions can be executed on a variety of hardware platforms and for interface to a variety of operating systems. In addition, the present invention is not described with reference to any particular programming language. It will be appreciated that a variety of programming languages may be used to implement the teachings of the invention as described herein. Furthermore, it is common in the art to speak of software, in one form or another (e.g., program, procedure, process, application, module, logic, etc.), as taking an action or causing a result. Such expressions are merely a shorthand way of saying that execution of the software by a machine causes the processor of the machine to perform an action or produce a result. It will be further appreciated that more or fewer processes may be incorporated into the methods illustrated in FIGS. 7, 9, 12-15 without departing from the scope of the invention and that no particular order is implied by the arrangement of blocks shown and described with respect to each of FIGS. 7, 9, 12-15.

Figure 16:
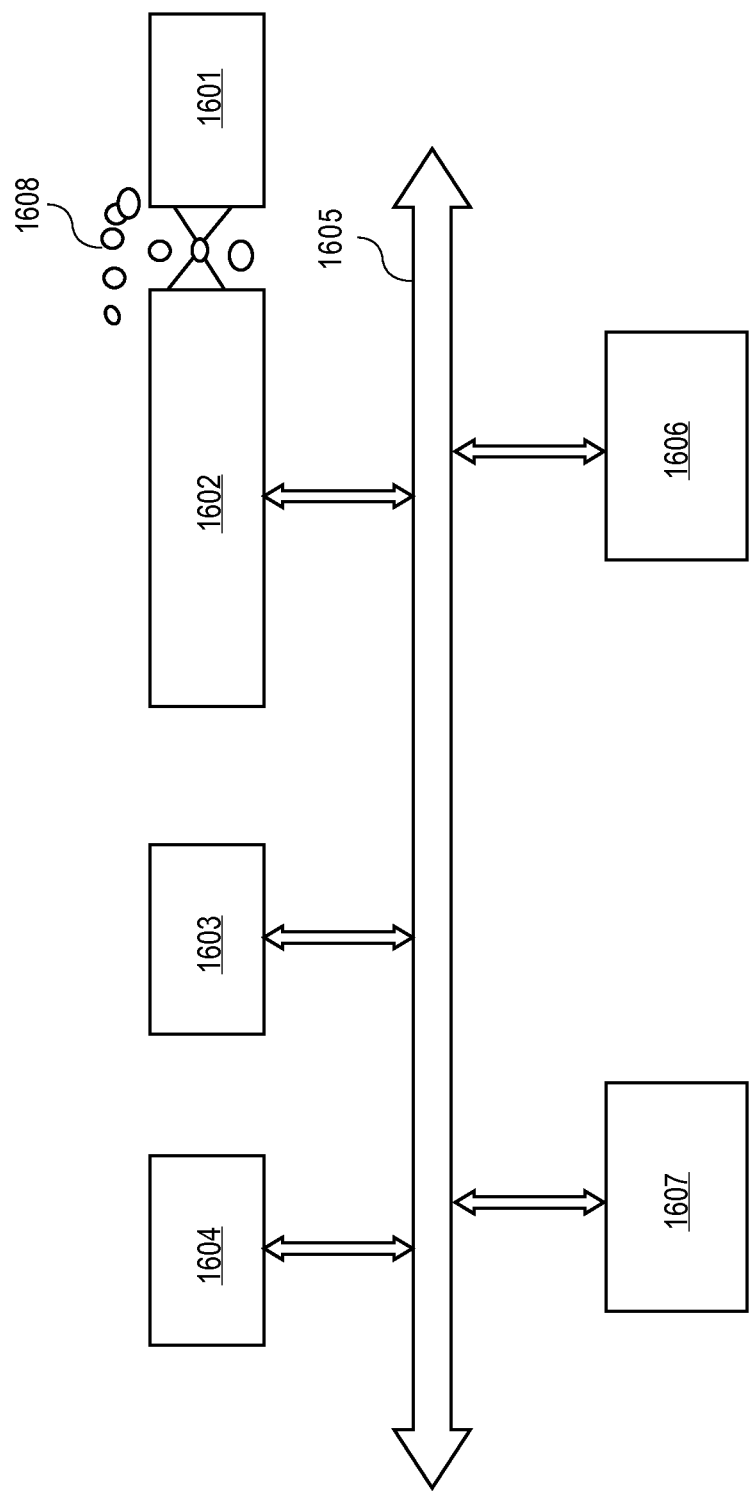
FIG. 16 illustrates one embodiment of a system to determine the size and velocity of the spherical objects that automatically sets up for instrument functions.

FIG. 16 shows one embodiment of a data and signal processing system to determine the size and velocity of the spherical objects that is automatically set up using methods described above. As shown on FIG. 16, system 1600 includes a transmitter 1601 to generate coherent laser beams crossed at an angle to form a sample volume to illuminate spherical particles 1608, as described above with respect to FIGS. 1 and 2. As shown in FIG. 16, system 1600 includes signal processor 600 that is coupled to receive the light scattered from the spherical objects 1608, as described above. Signal processor 600 includes a processing unit (not shown). For one embodiment, processing unit 605 can be a microprocessor, such as an Intel Pentium® microprocessor, Motorola Power PC® microprocessor, Intel Core™ Duo processor, AMD Athlon™ processor, AMD Turin™ processor, AMD Sempron™ processor, and any other microprocessor. For one embodiment, the processing unit of signal processor 600 includes a CPU, a microcontroller, a digital signal processor, a microprocessor, a general purpose computer, or any combination thereof. System 1600 can interface to external systems through a modem or network interface (not shown). It will be appreciated that the modem or network interface can be considered to be part of the system 1600. This interface can be an analog modem, ISDN modem, cable modem, token ring interface, satellite transmission interface, or other interfaces for coupling a computer system to other computer systems. As shown in FIG. 16, system 1600 further includes a memory 1603 coupled to the signal processor 600 by a bus 1605. Memory 1603 can be dynamic random access memory ("DRAM"), and can also include static RAM ("SRAM"). Bus 1605 couples signal processor 600 to memory 1603, to non-volatile storage 1604, to subsystem 1607, that can include GPU coupled by a display controller (not shown) to a display device (not shown), and to one or more subsystems 1606 that can include one or more I/O controllers (not shown) coupled to one or more I/O devices (not shown). The display controller controls in the conventional manner the display device which can be a cathode ray tube ("CRT") or liquid crystal display ("LCD"). The input/output devices can include a keyboard, disk drives, printers, a scanner, a digital camera, microphones, speakers, network or telephone communication interfaces, and other input and output devices including a mouse or other pointing device. The display controller and the I/O controller can be implemented with conventional well known technology. Non-volatile storage 1604 is often a magnetic hard disk, an optical disk, a diskette, CD-ROM, magnetic tape, DVD, ROM, Flash memory, or another form of storage of large amounts of data. Some of this data is often written, by a direct memory access process, into memory 1603 during execution of software in system 1600. One of skill in the art will immediately recognize that the terms "computer-readable medium" and "machine-readable medium" include any type of storage device that is accessible by the signal processor 600 and also encompass a carrier wave that encodes a data signal.

It will be appreciated that the data processing system 1600 is one example of many possible data processing systems which have different architectures. For example, personal computers based on an Intel microprocessor often have multiple buses, one of which can be an input/output (I/O) bus for the peripherals and one that directly connects the processing unit of signal processor 600 and the memory 1603 (often referred to as a memory bus). The buses can be connected together through bridge components that perform any necessary translation due to differing bus protocols. Bus 1605 can be Peripheral Component Interconnect ("PCI") bus, PCI-X, PCI Express, Universal Serial Bus ("USB"), IEEE 1394 bus (e.g., Firewire®), or any other bus known to one of ordinary skill in the art.

For one embodiment, signal processor 600 includes a photodetector section, an analog section, a digital section, and a digital/analog burst detector section, as described above with respect to FIGS. 3A, 4, 5, and 6. For one embodiment, signal processor 600 is incorporated in a single package. Signal processor 600 is configured to perform automated set-up methods as described above with respect to FIGS. 1-16. As shown in FIG. 16, memory 1603 and 1604 can store instructions and data for use by signal processor 600. For one embodiment, methods described above with respect to FIGS. 7, 9, 12-15 are implemented as a series of software routines run by system 1600. These software routines comprise instructions to be executed by processing unit of signal processor 600 in the system 1600. These instructions can be stored initially in memory 1604. It is to be appreciated that the series of instructions need not to be stored locally, and could be received from a remote storage device, such as a server on a network, via a network/communication interface. The instructions can be copied from memory 1604 to memory 1603 and then accessed and executed by the processing unit of the signal processor 600. Memory 1603 and memory 1604 may be used to store voltage-gain dependencies for photodetectors, attenuator settings, validation criteria for the measurement uncertainty, saturation and detection limits for gain settings, sample thresholds and ranges, probability thresholds, look-up tables for calibration, measured and processing data, as described above. Subsystem 1606 can include known in the art audio processing hardware and/or software to transform analog voice data to a digital form. For one embodiment, system 1600 moves automatically from one measurement location to another, performs automatic set-ups for measurement functions at each measurement location, and then acquires data using methods described above. For one embodiment, system 1600 is incorporated in a single package. For one embodiment, system 1600 is a system-on-chip ("SOC").

The above description of FIG. 16 is intended to provide an overview of the data processing system hardware and other operating components suitable for performing the methods of the invention described above, but is not intended to limit the applicable environments. Embodiments of the invention can be practiced with other computer system configurations, including hand-held devices, multiprocessor systems, microprocessor-based or programmable consumer electronics, network PCs, minicomputers, mainframe computers, and the like. The embodiments of the invention can also be practiced in distributed computing environments where tasks are performed by remote processing devices that are linked through a communications network, such as peer-to-peer network infrastructure.

Data processing system 1600 can be controlled by operating system software which includes a file management system, such as a disk operating system, which is part of the operating system software. One example of an operating system software with its associated file management system software is the family of operating systems known as Windows® from Microsoft Corporation of Redmond, Wash., and their associated file management systems. The file management system can be stored in non-volatile storage 1604 and can cause the processor unit of signal processor 600 to execute the various acts required by the operating system to input and output data and to store data in memory, including storing files on non-volatile storage 1604.

In the foregoing specification, embodiments of the invention have been described with reference to specific exemplary embodiments thereof. It will be evident that various modifications may be made thereto without departing from the broader spirit and scope of the invention. The specification and drawings are, accordingly, to be regarded in an illustrative sense rather than a restrictive sense.

What is claimed is:

1. A machine-implemented method to adjust a gain of a signal processing system, comprising:
setting a gain to a first value;
receiving signals;
measuring intensities of the signals; and
adjusting the gain to a second value based on the intensities, so that a smallest intensity of the signals is higher or equal to a detection level of the system and a largest intensity of the signals is less or equal to a saturation level of the system.

2. The machine-implemented method of claim 1, further comprising generating a histogram based on the intensities.

3. The machine-implemented method of claim 1, wherein the adjusting the gain includes adjusting a high voltage of a photomultiplier tube.

4. The machine-implemented method of claim 1, wherein the adjusting the gain to the second value includes attenuating optical signals in front of a photodetector.

5. A system, comprising:
means for setting a gain to a first value;
means for receiving signals;
means for measuring intensities of the signals; and
means for adjusting the gain to a second value based on the intensities, so that a smallest intensity of the signals is higher or equal to a detection level of the system and a largest intensity of the signals is less or equal to a saturation level of the system.

6. An article of manufacture, comprising:
a machine-accessible medium including data that, when accessed by a machine, cause the machine to perform operations comprising,
setting a gain to a first value;
receiving signals;
measuring intensities of the signals; and
adjusting the gain to a second value based on the intensities, so that a smallest intensity of the signals is higher or equal to a detection level of the system and a largest intensity of the signals is less or equal to a saturation level of the system.

7. The article of manufacture of claim 6, wherein the machine-accessible medium further includes data that cause the machine to perform operations, comprising
generating a histogram based on the intensities.

8. The article of manufacture of claim 6, wherein the adjusting the gain includes adjusting a high voltage of a photomultiplier tube.

9. The article of manufacture of claim 6, wherein the adjusting the gain includes attenuating optical signals in front of a photodetector.

* * * * *